United States Patent
Afanasiev et al.

(10) Patent No.: US 11,937,906 B2
(45) Date of Patent: Mar. 26, 2024

(54) SYSTEMS AND METHODS FOR MEASURING BIOLOGICAL METRICS AND BLOOD VESSEL GEOMETRY USING A MULTIPLE OPTICAL PATH PHOTOPLETHYSMOGRAPHY DEVICE

(71) Applicant: ALIO, INC, San Francisco, CA (US)

(72) Inventors: Andrei Afanasiev, Menlo Park, CA (US); Forrest Miller, Philadelphia, PA (US); Francis Honore, Longmont, CO (US); Anthony Flannery, Bainbridge Island, WA (US)

(73) Assignee: Alio, Inc., Broomfield, CO (US)

( * ) Notice: Subject to any disclaimer, the term of this patent is extended or adjusted under 35 U.S.C. 154(b) by 0 days.

(21) Appl. No.: 17/801,506

(22) PCT Filed: Apr. 11, 2021

(86) PCT No.: PCT/US2021/026763
§ 371 (c)(1),
(2) Date: Oct. 20, 2022

(87) PCT Pub. No.: WO2022/220784
PCT Pub. Date: Oct. 20, 2022

(65) Prior Publication Data
US 2024/0016403 A1  Jan. 18, 2024

(51) Int. Cl.
*A61B 5/1455* (2006.01)
*A61B 5/00* (2006.01)
(Continued)

(52) U.S. Cl.
CPC .......... *A61B 5/0261* (2013.01); *A61B 5/0022* (2013.01); *A61B 5/14535* (2013.01);
(Continued)

(58) Field of Classification Search
CPC ... A61B 5/0002; A61B 5/0205; A61B 5/0261; A61B 5/0022; A61B 5/1455;
(Continued)

(56) References Cited

U.S. PATENT DOCUMENTS 5,277,181 A   1/1994   Mendelson
5,575,285 A   11/1996  Takanashi et al.
(Continued)

FOREIGN PATENT DOCUMENTS

EP   1322216 B1   1/2015

OTHER PUBLICATIONS

PCT Search Report.

*Primary Examiner* — Chu Chuan Liu
(74) *Attorney, Agent, or Firm* — Rutan & Tucker, LLP

(57) ABSTRACT

Systems and methods for monitoring blood flow metrics using a patch of a flexible substrate configured to attach to an area of skin over a blood vessel. The patch includes a plurality of light sources arranged on the substrate to form a matrix and a row of photodetectors disposed on the substrate substantially in parallel with the rows of LEDs. The patch includes an optical signal interface configured to drive each light source and to input an intensity signal at one of the photodetectors. The intensity signals are used to determine AC and DC components corresponding to each optical path. AC to DC component ratios are calculated for each optical path and used to determine ratio-of-ratio values. At least a subset of the ratio-of-ratio values are used to determine a biological metric or a cross-sectional area of the blood vessel.

14 Claims, 18 Drawing Sheets

(51) Int. Cl.
*A61B 5/026* (2006.01)
*A61B 5/145* (2006.01)

(52) U.S. Cl.
CPC ...... *A61B 5/14551* (2013.01); *A61B 5/14552* (2013.01); *A61B 5/6833* (2013.01)

(58) Field of Classification Search
CPC ............ A61B 5/14551; A61B 5/14552; A61B 5/14535; A61B 5/6833
See application file for complete search history.

(56) References Cited

U.S. PATENT DOCUMENTS

| | | | | |
|---|---|---|---|---|
| 5,987,351 | A | * | 11/1999 | Chance .............. A61B 5/14552 600/476 |
| 8,203,704 | B2 | | 6/2012 | Merritt |
| 8,423,105 | B2 | | 4/2013 | Genoe |
| 2002/0042558 | A1 | * | 4/2002 | Mendelson .......... A61B 5/1455 600/323 |
| 2013/0261415 | A1 | * | 10/2013 | Ashe ................. A61B 5/14552 600/323 |
| 2016/0334332 | A1 | * | 11/2016 | Magnussen ........ A61B 5/14546 |
| 2021/0393176 | A1 | * | 12/2021 | Khan ................. A61B 5/14551 |

\* cited by examiner

550

| $RoR_{11} = \frac{R_{11}}{R_{11}}$ | $RoR_{12} = \frac{R_{12}}{R_{12}}$ | $RoR_{13} = \frac{R_{13}}{R_{13}}$ |
|---|---|---|
| $RoR_{21} = \frac{R_{21}}{R_{11}}$ | $RoR_{22} = \frac{R_{22}}{R_{12}}$ | $RoR_{23} = \frac{R_{23}}{R_{13}}$ |
| $RoR_{31} = \frac{R_{31}}{R_{11}}$ | $RoR_{32} = \frac{R_{32}}{R_{12}}$ | $RoR_{33} = \frac{R_{33}}{R_{13}}$ |
| $RoR_{41} = \frac{R_{41}}{R_{11}}$ | $RoR_{42} = \frac{R_{42}}{R_{12}}$ | $RoR_{43} = \frac{R_{43}}{R_{13}}$ |
| $RoR_{51} = \frac{R_{51}}{R_{11}}$ | $RoR_{52} = \frac{R_{52}}{R_{12}}$ | $RoR_{53} = \frac{R_{53}}{R_{13}}$ |

560

| $RoR_{11} = \frac{R_{11}}{R_{11}}$ | $RoR_{12} = \frac{R_{12}}{R_{12}}$ | $RoR_{13} = \frac{R_{13}}{R_{13}}$ |
|---|---|---|
| $RoR_{21} = \frac{R_{11}}{R_{21}}$ | $RoR_{22} = \frac{R_{12}}{R_{22}}$ | $RoR_{23} = \frac{R_{13}}{R_{23}}$ |
| $RoR_{31} = \frac{R_{21}}{R_{31}}$ | $RoR_{32} = \frac{R_{22}}{R_{32}}$ | $RoR_{33} = \frac{R_{23}}{R_{33}}$ |
| $RoR_{41} = \frac{R_{31}}{R_{41}}$ | $RoR_{42} = \frac{R_{32}}{R_{42}}$ | $RoR_{43} = \frac{R_{33}}{R_{43}}$ |
| $RoR_{51} = \frac{R_{41}}{R_{51}}$ | $RoR_{52} = \frac{R_{42}}{R_{52}}$ | $RoR_{53} = \frac{R_{43}}{R_{53}}$ |

FIG. 5C $R_{redr,c}$ ──721                                   $R_{IRr,c}$ ──731

──740

| $R_{COMP11} = \dfrac{R_{red11}}{R_{IR11}}$ | $R_{COMP12} = \dfrac{R_{red12}}{R_{IR12}}$ | $R_{COMP13} = \dfrac{R_{red13}}{R_{IR13}}$ |
|---|---|---|
| $R_{COMP21} = \dfrac{R_{red21}}{R_{IR21}}$ | $R_{COMP22} = \dfrac{R_{red22}}{R_{IR22}}$ | $R_{COMP23} = \dfrac{R_{red23}}{R_{IR23}}$ |
| $R_{COMP31} = \dfrac{R_{red31}}{R_{IR31}}$ | $R_{COMP32}\, \dfrac{R_{red32}}{R_{IR32}}$ | $R_{COMP33} = \dfrac{R_{red33}}{R_{IR33}}$ |
| $R_{COMP41} = \dfrac{R_{red41}}{R_{IR41}}$ | $R_{COMP42} = \dfrac{R_{red42}}{R_{IR42}}$ | $R_{COMP43} = \dfrac{R_{red43}}{R_{IR43}}$ |
| $R_{COMP51} = \dfrac{R_{red51}}{R_{IR51}}$ | $R_{COMP52} = \dfrac{R_{red52}}{R_{IR52}}$ | $R_{COMP53} = \dfrac{R_{red53}}{R_{IR53}}$ |

──750

| $RoR_{11} = \dfrac{R_{COMP11}}{R_{COMP11}}$ | $RoR_{12} = \dfrac{R_{COMP12}}{R_{COMP12}}$ | $RoR_{13} = \dfrac{R_{COMP13}}{R_{COMP13}}$ |
|---|---|---|
| $RoR_{21} = \dfrac{R_{COMP21}}{R_{COMP11}}$ | $RoR_{22} = \dfrac{R_{COMP22}}{R_{COMP12}}$ | $RoR_{23} = \dfrac{R_{COMP23}}{R_{COMP13}}$ |
| $RoR_{31} = \dfrac{R_{COMP31}}{R_{COMP11}}$ | $RoR_{32} = \dfrac{R_{COMP32}}{R_{COMP12}}$ | $RoR_{33} = \dfrac{R_{COMP33}}{R_{COMP13}}$ |
| $RoR_{41} = \dfrac{R_{COMP41}}{R_{COMP11}}$ | $RoR_{42} = \dfrac{R_{COMP42}}{R_{COMP12}}$ | $RoR_{43} = \dfrac{R_{COMP43}}{R_{COMP13}}$ |
| $RoR_{51} = \dfrac{R_{COMP51}}{R_{COMP11}}$ | $RoR_{52} = \dfrac{R_{COMP52}}{R_{COMP12}}$ | $RoR_{53} = \dfrac{R_{COMP53}}{R_{COMP13}}$ |

*FIG. 7C*

| | | 760 |
|---|---|---|
| $RoR_{11} = \dfrac{R_{COMP11}}{R_{COMP11}}$ | $RoR_{12} = \dfrac{R_{COMP12}}{R_{COMP12}}$ | $RoR_{13} = \dfrac{R_{COMP13}}{R_{COMP13}}$ |
| $RoR_{21} = \dfrac{R_{COMP11}}{R_{COMP21}}$ | $RoR_{22} = \dfrac{R_{COMP12}}{R_{COMP22}}$ | $RoR_{23} = \dfrac{R_{COMP13}}{R_{COMP23}}$ |
| $RoR_{31} = \dfrac{R_{COMP21}}{R_{COMP31}}$ | $RoR_{32} = \dfrac{R_{COMP22}}{R_{COMP32}}$ | $RoR_{33} = \dfrac{R_{COMP23}}{R_{COMP33}}$ |
| $RoR_{41} = \dfrac{R_{COMP31}}{R_{COMP41}}$ | $RoR_{42} = \dfrac{R_{COMP32}}{R_{COMP42}}$ | $RoR_{43} = \dfrac{R_{COMP33}}{R_{COMP43}}$ |
| $RoR_{51} = \dfrac{R_{COMP41}}{R_{COMP51}}$ | $RoR_{52} = \dfrac{R_{COMP42}}{R_{COMP52}}$ | $RoR_{53} = \dfrac{R_{COMP43}}{R_{COMP53}}$ |

| $RoR_{11} = \frac{R_{11}}{R_{12}}$ | $RoR_{12} = \frac{R_{12}}{R_{12}}$ | $RoR_{13} = \frac{R_{13}}{R_{12}}$ |
|---|---|---|
| $RoR_{21} = \frac{R_{21}}{R_{22}}$ | $RoR_{22} = \frac{R_{22}}{R_{22}}$ | $RoR_{23} = \frac{R_{23}}{R_{22}}$ |
| $RoR_{31} = \frac{R_{31}}{R_{32}}$ | $RoR_{32} = \frac{R_{32}}{R_{32}}$ | $RoR_{33} = \frac{R_{33}}{R_{32}}$ |
| $RoR_{41} = \frac{R_{41}}{R_{42}}$ | $RoR_{42} = \frac{R_{42}}{R_{42}}$ | $RoR_{43} = \frac{R_{43}}{R_{42}}$ |
| $RoR_{51} = \frac{R_{51}}{R_{52}}$ | $RoR_{52} = \frac{R_{52}}{R_{52}}$ | $RoR_{53} = \frac{R_{53}}{R_{52}}$ |

890

| $RoR_{11} = \frac{R_{11}}{R_{RefPeak}}$ | $RoR_{12} = \frac{R_{12}}{R_{RefPeak}}$ | $RoR_{13} = \frac{R_{13}}{R_{RefPeak}}$ |
|---|---|---|
| $RoR_{21} = \frac{R_{21}}{R_{RefPeak}}$ | $RoR_{22} = \frac{R_{22}}{R_{RefPeak}}$ | $RoR_{23} = \frac{R_{23}}{R_{RefPeak}}$ |
| $RoR_{31} = \frac{R_{31}}{R_{RefPeak}}$ | $RoR_{32} = \frac{R_{32}}{R_{RefPeak}}$ | $RoR_{33} = \frac{R_{33}}{R_{RefPeak}}$ |
| $RoR_{41} = \frac{R_{41}}{R_{RefPeak}}$ | $RoR_{42} = \frac{R_{42}}{R_{RefPeak}}$ | $RoR_{43} = \frac{R_{43}}{R_{RefPeak}}$ |
| $RoR_{51} = \frac{R_{51}}{R_{RefPeak}}$ | $RoR_{52} = \frac{R_{52}}{R_{RefPeak}}$ | $RoR_{53} = \frac{R_{53}}{R_{RefPeak}}$ |

FIG. 8C

SYSTEMS AND METHODS FOR MEASURING BIOLOGICAL METRICS AND BLOOD VESSEL GEOMETRY USING A MULTIPLE OPTICAL PATH PHOTOPLETHYSMOGRAPHY DEVICE

BACKGROUND

A significant amount of effort has been devoted recently in the medical diagnostics industry to the development of portable, even wearable, diagnostics devices configured to assist medical practitioners in monitoring patients remotely. Such remote monitoring would ideally provide a practitioner with data not otherwise available, such as trendline data, and would reduce visits by patients to clinics, laboratories or other testing centers. This objective has become even more critical this past year in the face of the COVID-19 pandemic that has gripped the entire world. The COVID-19 pandemic has strained the healthcare infrastructure. The rapid spread of the virus has pushed hospitals past their breaking point. Overcrowding, overworked staff and shortages of resources have made it difficult for the healthcare system to attend to not just COVID-19 patients, but patients requiring other types of treatment.

This situation is particularly difficult for vulnerable patient populations, such as patients having chronic illnesses. Vulnerable patient populations are at the highest risk for severe symptoms if they contract COVID. These patients also must make frequent visits with their care providers to monitor, treat and manage their chronic illnesses. Dialysis patients, for example, are at a very high risk since many still must come in for dialysis 3× per week and have a high number of comorbidities to manage including diabetes, heart failure and anemia.

A number of telehealth services are being utilized to enable the transition of care from the hospital to home. However, telehealth visits today only provide clinicians access to subjective data, rather than objective data. For vulnerable populations there is currently no way to replicate or supplement in-clinic testing in their homes for the most significant issues they encounter. In most cases, a prognostic screening tool (as opposed to a diagnostic test) would be sufficient to supplement and reduce the in-clinic testing burden. An accurate at-home screening system would reduce in-clinic testing burden and exposure risk for patients and physicians. With automated, at-home screening, in-clinic testing could be directed to occur only when indicated by significant changes detected by the at-home screening.

Core metrics that would benefit from remote, noninvasive monitoring include hemoglobin and hematocrit (Hb/Hct). One example of the types of patients that can benefit from improved noninvasive monitoring is dialysis patients. Many dialysis patients typically undergo monthly blood draws to test for Hb/Hct levels. These patients are often taking erythropoietin (EPO) to manage their anemia alongside their dialysis treatment. These patients' Hb/Hct levels must be closely monitored so their EPO dosage and/or dialysis dose can be titrated when needed. The consequences of over-dialyzing are severe—patients can become hypotensive, causing hospitalization and even death.

Since blood draws are carried out infrequently, physicians rely on patients self-reporting symptoms and/or the judgement of dialysis center staff to identify when patients may need an adjustment in dosage. The lack of objective measures for this critical input in the dialysis process has contributed to high rates of hospitalization and mortality amongst dialysis patients.

Supplementing monthly blood draws with a more frequent assessment of Hb/Hct levels to alert clinicians to a potential issue would be desirable. This has led to the adoption of a number of Hb/Hct measurement devices to supplement monthly blood draws with weekly in-clinic tests. While these tools for Hb/Hct monitoring suffer from high error, their ease-of-use compared to blood draw enables trendlining of Hb/Hct which provides additional clinical insight.

Currently available tools for HB/Hct monitoring tend to exhibit errors that may be significant and have not replaced the need for patients to visit testing centers for blood draws. More accurate HB/Hct monitoring would allow for more accurate trendlining and may reduce the need for hospital visits for not only dialysis patients, but patients with other conditions as well.

SUMMARY

In view of the above, systems and methods are provided for monitoring blood flow metrics using multiple optical paths from a plurality of light sources and light detectors. In one example, a patch of a flexible substrate is configured to attach to an area of skin over a blood vessel. A plurality of light emitting diodes (LEDs) arranged on the substrate to form a R×C matrix and a row of C photodetectors (PDs) disposed on the substrate substantially in parallel with R rows of LEDs extending to form C columns substantially co-linear with each photodetector. An optical signal interface is mounted on the substrate and configured to drive each LED for an on-period and to input an optical signal at one of the photodetectors during the on-period. An intensity measurement is received for an optical path, $OP_{rc}$, formed by LEDs in rows r=1 to R in columns c=1 to C and the photodetector receiving the optical signal. A processing system comprising a memory for storing program instructions for execution by the processing system is configured, when executing the instructions, to:

a. receive a plurality of intensity measurements, $I_{rc}$, corresponding to the optical paths, $OP_{rc}$, for a period of time to receive a plurality of intensity measurements for each optical path;

b. determine an AC component, $I_{rc,AC}$, and a DC component, $I_{rc,DC}$, as a function of the plurality of intensity measurements, $I_{rc}$, for each optical path, $OP_{rc}$, over the period of time;

c. determine an AC-to-DC component ratio, $$R_{r,c} = \frac{I_{rc,AC}}{I_{rc,DC}},$$

for each optical path;

d. determine a plurality of ratio-of-ratios, RoR values, by dividing a first plurality of selected AC-to-DC component ratios by a second plurality of selected AC to DC component ratios; and e. using at least a subset of the RoR values to determine a biological metric.

In one aspect, the plurality of LEDs is a plurality of infrared (IR) LEDs emitting infrared light. The memory of the processing system includes program instructions for execution by the processing system to, in using at least the subset of RoR values to determine the biological metric, where the biological metric is hematocrit concentration, Hct, determined using: Hct=F(RoR'), where F is a transfer function that correlates a range of RoR values to a range of hematocrit concentration values based on reference hematocrit concentrations determined from a plurality of reference RoR values measured using a reference hematocrit measurement system, and where RoR' is at least a subset of RoR values.

DESCRIPTION OF THE DRAWINGS

FIG. 5C depicts tables of ratio-of-ratio (RoR) values illustrating alternative schemes for the determination of RoRs.

FIGS. 7B-7D are flow diagrams and matrices illustrating examples of methods for determining ratios of ratios for the plurality of optical paths at two wavelengths.

FIG. 8C depicts two examples of matrices of RoR values that may be used to determine a blood vessel cross-sectional area.

DETAILED DESCRIPTION

Figure 1:
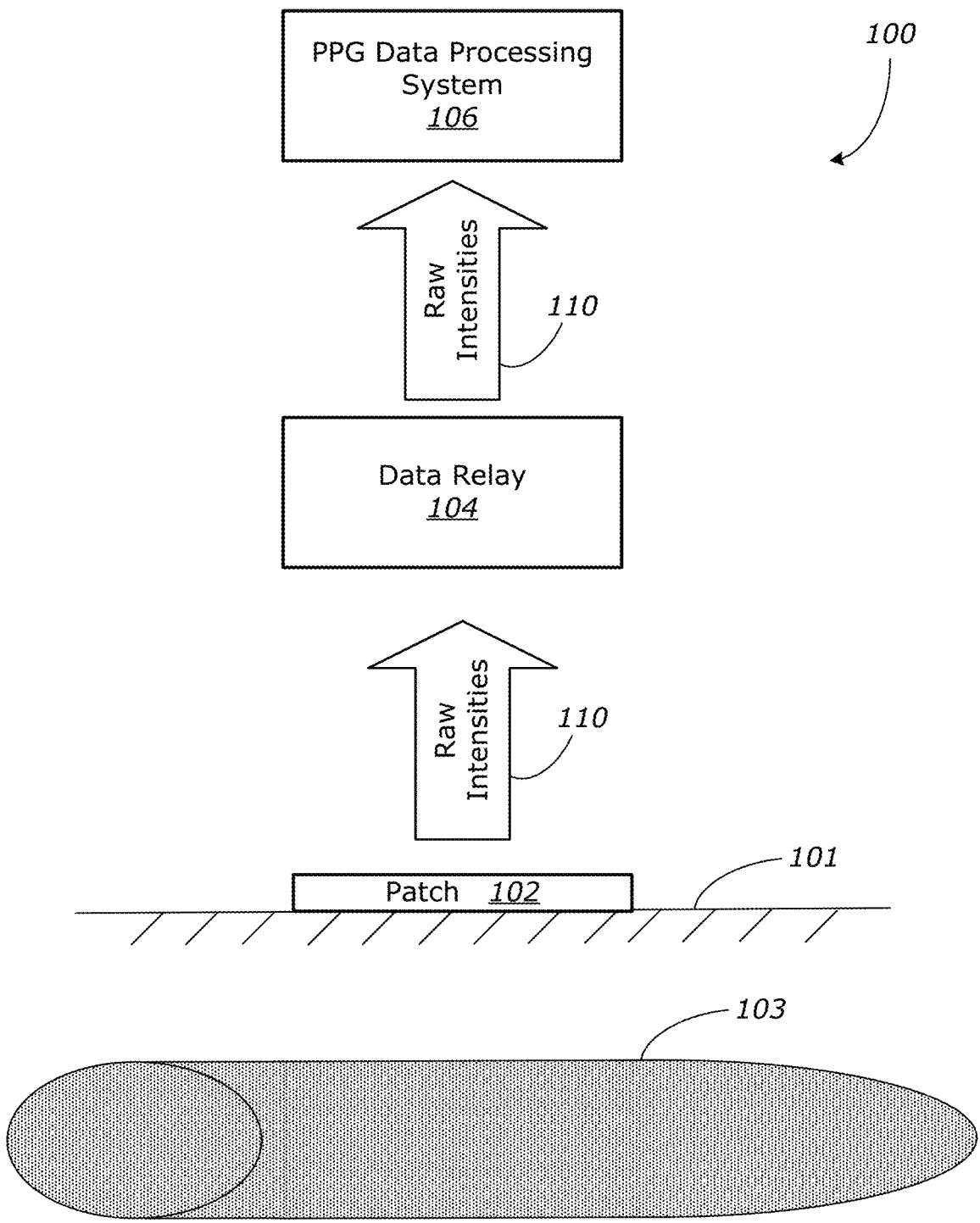
FIG. 1 is a block diagram of an example implementation of a system for determining biological metrics.

The following describes systems and methods for measuring biological metrics and a cross-sectional area of an underlying blood vessel. In an example implementation, a system includes a patch configured to be affixed to an area of skin above a blood vessel. The patch includes a plurality of light emitting diodes ("LEDs") and a plurality of photodetectors. The LEDs may be arranged in an R rows by C columns grid such that each of C photodetectors is placed collinearly with a column of R rows. The matrix of LEDs and photodetectors is arranged to cover an area above the blood vessel so that the light from the LEDs form optical paths between the LEDs and the photodetectors that substantially intersect with the blood vessel.

The LEDs may emit light at any suitable wavelength corresponding to the biological metrics to be measured. For example, hematocrit may be measured using infrared (IR) light. Some measurements, such as, for example, oxygen saturation, may be measured using optical measurements from red and IR light. LED wavelengths may be selected based on the interaction of the light and properties of the tissue for the metric being measured. For example, IR light is selected for measuring Hct because the intensity of IR signal measured through the blood is a function of the interaction with the hemoglobin in the red blood cells. This disclosure focuses on the measurement of hematocrit (Hct), hemoglobin (Hgb), and oxygen saturation (SpO2). However, other metrics may be performed using light at similar wavelengths using example techniques described below.

In example implementations, a system is configured to calculate Hct by applying a transfer function to a photoplethysmography (PPG) parameter termed "ratio-of-ratios." A "ratio-of-ratios," or RoR, refers to a ratio of two values which are themselves ratiometric. For each of two LED-photodiode pairs where the infrared LEDs are positioned at different distances from the same photocliode, the ratio of the signal's amplitude is divided by the DC value of the signal. This AC/DC value is alternately called the diffuse reflectance or perfusion index, depending on the application for which the PPG sensor is being used.

In example implementations, a patch may be configured to perform PPG measurements using a plurality of light sources arranged in an array having rows and columns and extending from a row of light detectors substantially in parallel with the rows of light sources. Each light source may form an optical path with each light detector. For each optical path, an AC/DC value, or a perfusion index, may be determined. Multiple channels may be defined to correspond with the multiple light detectors in a PPG grid.

PPG grids are described below using photodetectors as light detectors and light emitting diodes (LEDs) as light sources, without intending to limit light sources or light detectors to any specific device. The LEDs in any example PPG grid may include LEDs of any suitable wavelength, which may depend on the biological metric being measured. LEDs with multiple wavelengths may be used in the PPG grid, which again may depend on the biological metric being measured.

The PPG grids described below include three photodetectors in a row and five rows of LEDs extending substantially in parallel with the photodetectors. However, the PPG grids may be implemented using any suitable number of photodetectors and any suitable number of LEDs. The number of photodetectors and LEDs as well as the spacing between the components may depend on factors such as level of complexity desired, expected geometry of the blood vessel, approximate depth of the blood vessel, and other factors. In general, the geometry of the PPG grid may be configured to obtain a maximum interaction of light signals with the blood flowing in a target blood vessel.

A plurality of RoRs may be computed by dividing the AC/DC value from an optical path for one LED by the AC/DC value from an optical path for another LED. In some examples, the AC/DC value for optical paths corresponding to each nearer LED may be divided by the AC/DC value of the optical path corresponding to the next further LED. In some examples, the AC/DC value for optical paths corresponding to a selected LED may be used as a reference and used in determining RoRs corresponding to each LED.

In general, RoRs may be determined in a manner that can achieve analytical advantages in determining blood metrics, such as Hct, Hgb, SpO2, and others, including for example, geometric metrics of the blood vessel. Examples of using PPG grids and RoRs calculated from PPG grids to determine Hct and SpO2 are described below with reference to FIGS. 5A-5D, 6A-6B, and 7A-7B. Examples of using RoRs to determine blood vessel geometry are described below with reference to FIGS. 8A and 8B.

In some example implementations, RoRs may be determined for optical paths in the column of LEDs corresponding to each photodetector. The RoRs in columns may be analyzed to determine, for example, an optimum column of RoRs to use to determine the blood metric. In another example, a plurality of RoRs determined in columns of RoRs may be used to determine the blood metric. The plurality of RoRs in a column or in multiple columns may be curve fit according to a transfer function for the selected blood metric. In another example, a plurality of the RoRs may be surface fit to a transfer function.

It is noted that the values of the RoRs for each channel may depend on the position of each column of LEDs over the blood vessel. The placement of the patch on the skin over the blood vessel may not quite result in an exact alignment of the blood vessel with any of the channels. The optical paths formed in each channel may converge only partially with the blood vessel. The RoR values may be used to determine an optimum column from which to determine the desired blood metric. In one example, the optimum column of LEDs may be identified as the column having the highest magnitude RoR value or values. In another example, the RoRs in columns may be compared with a measured peak RoR and the RoR value or values from the column with the highest percent RoR or RoRs may be used in determining the blood metric.

An optimum single RoR, RoR', may be determined and used in a transfer function to determine an Hct concentration according to: [Hct]=$f$(RoR'). The transfer function may be derived from an analysis of a mathematical construction of the convergence of the optical paths with the blood vessel. In one example, the transfer function fits a second-order polynomial to the RoR' parameter: Hct=$aR^2+bR+c$, where parameters a, b, and c are determined by curve fitting reference values of R=RoR to determine known values of Hct. Further enhancements can be taken by using look up tables for different ratios to accommodate for any non-linearities across the range of hematocrit concentrations desired.

In some examples, the Hct may be determined using multiple RoR values. For example, an optimum column of RoR values may be used in a transfer function expressed as: [Hct]=$f$(RoR|optimum column). In this example, the RoR values in the column deemed the optimum column may be fit to a multivariable curve function determined using known regression analysis techniques. In other examples, the Hct may be determined using [Hct]=$f$(All RoR values). The set of RoR values may be fit to a function using regression analysis techniques. In other examples, the transfer function may use a surface fitting technique.

The above illustrates how an Hct value may be determined in example implementations. Similar techniques may be implemented for determining other blood metrics. For example, with respect to a determination of the oxygen saturation, a similar analysis incorporating RoRs may be performed, but using two wavelengths. Example implementations are described in more detail with reference to FIGS. 6A-6C.

The calculation of RoRs from intensity measurements on a PPG device may also be used to determine a cross-sectional area of the blood vessel being interrogated with the optical signals. In an example implementation, RoRs may be determined across rows of optical paths measured by the patch. An optimum row of RoRs may be identified and the values may be compared with curvilinear relationships between reference RoRs and a percent of ratios of distances from the center of the blood vessel. Examples of the use of row RoRs for determining geometric characteristics of the blood vessel are described below with reference to FIG. 7.

Referring to FIG. 1, a system 100 for monitoring blood flow metrics includes patch 102 mounted on an area of skin 101 above a target blood vessel 103. The patch 102 may be configured to measure optical signals using LEDs and photodetectors disposed on the patch. The optical signals, typically intensity values, may be communicated as raw intensity signals to a PPG data processing system 106. In some implementations, some or all of the data processing for obtaining the biological metrics may be performed on the patch 102. Some signal processing, such as noise cancellation, filtering, SNR reduction, etc. may be performed on the patch 102 and communicated to the PPG data processing system 106 as raw intensities.

It is noted that the patch 102 may be configured for use by a patient located remotely from a medical office or testing center. That is, the patient may be at home when data transfers are made to the PPG data processing system 106 or to a location that is configured to receive the results of the measurements. Such data transfers may use WiFi, the cellular communication infrastructure, or any other suitable communications medium for transferring the data to the PPG data processing system 106 and then to the doctor, or medical personnel that needs the results.

In an example implementation, the PPG data processing system 106 operates as a cloud service. A data relay 104 may be used to mediate the data transfer between the patch 102 and the PPG data processing system 106. The data relay 104 for example, may operate as a smartphone app, which may format reports of the data to communicate to the PPG data processing system 106, which may operate as a cloud service. The data relay 104 may in general be a specially configured bridge-type networked component, or any other suitable networked component configured to receive the raw intensity signals and to communicate the raw intensity signals to the PPG data processing system 106.

It is noted that the data relay 104 in FIG. 1 may be portable, such as with a smartphone, or intended to be located in a room frequented by the patient wearing the patch 102. The data relay 104 may be configured to establish an on-demand connection when substantially co-located with the patch 102 and to communicate data between the patch 102 and the PPG data processing system 106 during the connection.

Figure 2A:
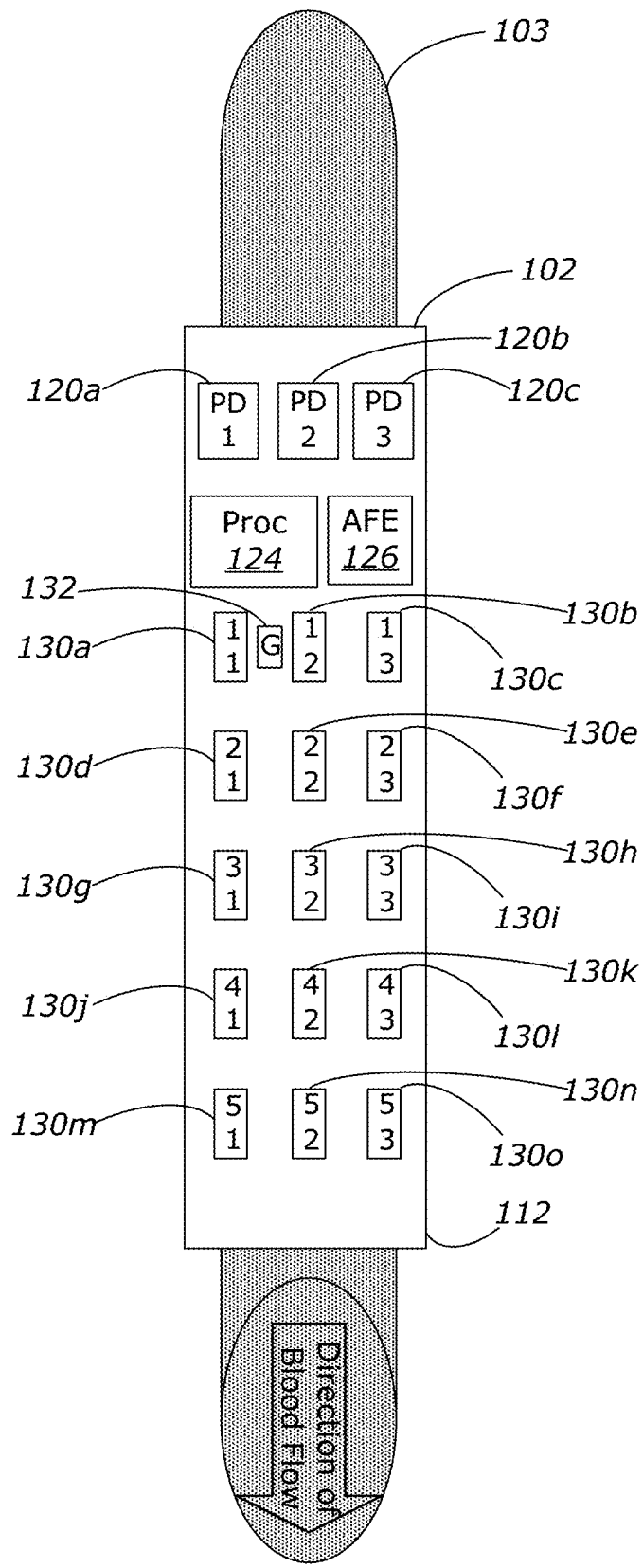
FIG. 2A is an example implementation of a patch configured to generate a plurality of optical paths for measuring biological metrics.

Referring to FIG. 2A, the patch 102 may be implemented as a flexible substrate 112 configured to attach to an area of skin 101 over a blood vessel 103. The substrate may be made of any suitable material capable of supporting electronic components embedded thereon. One surface may be treated to adhere to skin and may also include ports to allow light to exit the substrate from the LEDs into the skin and additional ports to allow light to enter to the photodetectors from the skin. The patch 102 includes a plurality of LEDs 130a-o arranged on the substrate to form a R×C matrix and a row of C photodetectors 120a-c disposed on the substrate substantially in parallel with the R rows of LEDs extending to form C columns substantially co-linear with each photodetector 120.

An optical signal interface (shown in FIG. 2A as an analog front-end (AFE)) 126 is mounted on the substrate 112 and configured to drive each LED 130 for an on-period and to input an optical signal at one of the photodetectors 120 during the on-period to receive an intensity measurement for an optical path, OPrc, formed by LEDs 130 in rows r=1 to R in columns c=1 to C and the photodetector 120 receiving the optical signal. The on-period of time is sufficient to obtain a single intensity from an optical path. Each LED 130 forms at least one optical path with the photodetectors 120. In one example implementation, the optical paths are formed between each LED 130 in a column, each of which extends from one of the photodetectors 120. The plurality of optical paths for each LED 130 each column forms a channel of optical paths for each photodetector 120.

The system 100 includes a processing system comprising a memory for storing program instructions for execution by the processing system to determine the biological metrics and the cross-sectional area of the blood vessel 103. The processor 124 may also perform other functions as part of a processing system that determines the biological metrics from the intensities. A processor 124 may be provided on the patch 102 to control the activation of the LEDs 130 and the reading of the intensities from the photodetectors 120. The processor 124 may control the generation of the optical paths to read raw intensities, may perform signal processing functions, and may communicate the raw intensities to the PPG processing system 106 to perform additional functions to derive the biological metrics from the intensities. In some implementations, the processor 124 may also be configured to perform the functions that determine the biological metrics. The extent to which the processor 124 on the patch performs functions to determine the biological metrics depends on the processing power and the electrical power capabilities of the processor mounted on the patch 102 as well as the amount of memory that can be accommodated on the patch 102. The patch 102 may be powered by a battery, which would lose charge and require recharging or the patch to be disposed and replaced.

The patch 102 in FIG. 2A may be powered by a battery. For purposes of clarification in the description below, the processor 124 may be implemented as part of the processing system (along with the PPG data processing system 106) that determines the biological properties and the cross-sectional area of the blood vessel 103. In an example implementation, the processor 124 on the patch 102 controls the measurement of optical intensities and communicates the raw intensities to the PPG data processing system 106 for performance of the additional steps to calculate the biological metrics.

In an example implementation, the PPG processing system 106, which may be a cloud-based service, receives a plurality of intensity measurements, $I_{rc}$, corresponding to the optical paths, $OP_{rc}$, for a period of time to receive a plurality of intensity measurements for each optical path. The period of time over which the intensities are received by the PPG processing system 106 may be sufficient for several heart beats to have pumped blood through the blood vessel. The processing system 106 analyzes the raw intensities for each optical path over time to detect changes in intensity as the blood flows in the blood vessel 103 due to the heart beats.

The PPG processing system 106 may determine an AC component, $I_{rc,AC}$, and a DC component, $I_{rc,DC}$, as a function of the plurality of intensity measurements, $I_{rc}$, for each optical path, $OP_{rc}$, over the period of time. The intensity measurements may be analyzed to correspond with any electrocardiogram (ECG) signals generated as the heart pumps blood. The correspondence with the ECG signals may be determined from the changes in intensity over time and compared with a pattern of expected intensity changes due to the heart beats. The calculation of AC-to-DC components is described in more detail below with reference to FIGS. 5A and 5B. Once the AC and DC components for each optical path are determined, a ratio of AC-to-DC components, $$R_{r,c} = \frac{I_{rc,AC}}{I_{rc,Dc}},$$

may be determined for each optical path. The ratios of AC-to-DC components may then be used to determine a plurality of ratio-of-ratios, RoR values, by dividing a first plurality of selected AC-to-DC component ratios by a second plurality of selected AC to DC component ratios. The first plurality of selected AC-to-DC component ratio and the second plurality of selected AC-to-DC component ratio may be selected so as to generate RoR values that may be indicative of optical paths with a best signal or signals from which to obtain optical measurements. Selected RoR values may then be used to determine blood metrics and/or geometric properties of the blood vessel as described below.

The patch 102 depicted in FIG. 2A includes R=5 rows of LEDs arranged in C=3 columns. The number of rows, R, and the number of columns, C, in any specific implementation may each be any suitable number and may depend on the typical approximate size of the blood vessel to be interrogated. Similarly, the distance between the channels, or the columns of LEDs and photodetectors, may depend on the typical approximate size of the blood vessel to be interrogated.

Figure 2B:
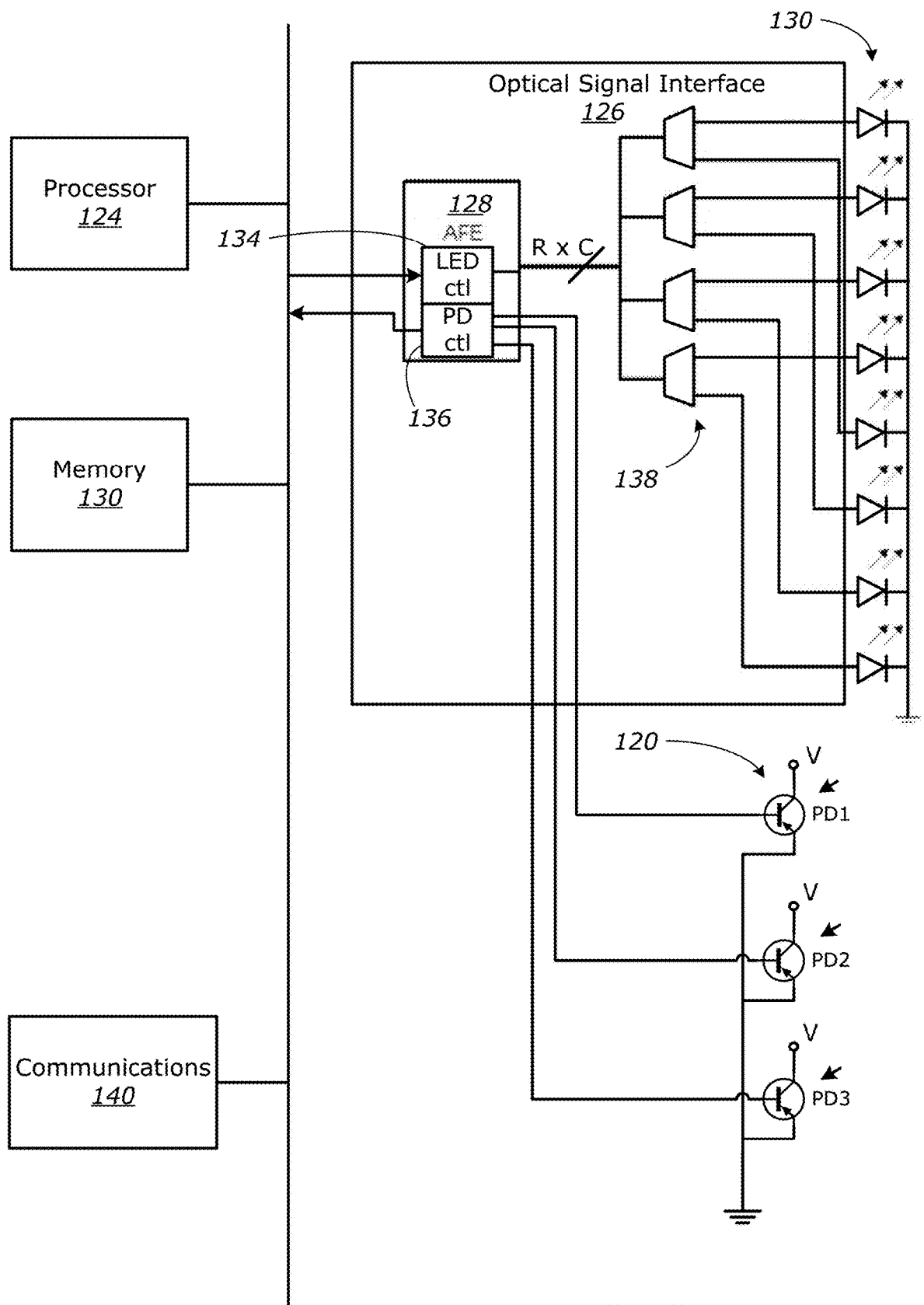
FIG. 2B is a schematic diagram of an example system disposed on an example patch for measuring biological metrics.

FIG. 2B is a schematic diagram of an example system disposed on an example patch 102 for measuring biological metrics. It is noted that example implementations of the patch 102 may include additional components for performing other features, such as an accelerometer to detect motion, an audio pickup for detecting a heart rate, a single lead sensor for performing ECG, etc. The example implementation in FIG. 2B includes the processor 124, a storage element (memory) 130, a communications interface 140, an optical signal interface 126, the plurality of LEDs 130, and the plurality of photodetectors 120.

The processor 126 may be any suitable processing element. In an example implementation, the processor 126 controls the reading of optical signals and the activation of LEDs according to an excitation pattern. The processor 126 then communicates the optical signals, raw intensity values, to the PPG data processing system 106 via the communication interface 140. The communication interface 140 may be any suitable wireless interface, such as for example, Bluetooth™, Bluetooth™ low energy (BLE™), WiFi signals, or other suitable alternatives. The wireless interface may be configured to communicate with the PPG data processing system 106 directly, such as for example, via a cellular communication system, or Wi-Fi connected to the Internet. In an example implementation, the wireless interface on the patch 102 communicates with the PPG data processing system 106 via the data relay 104 (FIG. 1). The data relay 104 allows for a less complex interface between the communications interface 140 on the patch and the data relay 104, such as via BLE™, thereby reducing the power demand on the patch 102. The data relay 104 may then connect to the PPG data processing system 106 on a cloud server, or another suitable networked component using a cellular network, a WiFi interface connected to the Internet, or any other suitable networking infrastructure.

The processor 124 executes instructions stored in memory 130. The memory 130 may also be used to store raw data collected from the photodetectors 120, and data resulting from any signal processing for which the processor 124 is programmed to perform. The processed data may be communicated to the PPG data processing system 106 as raw intensity signals.

The processor 124 may operate over a bus 150 embedded in the patch 102. The optical signal interface 126 may be connected to the bus 150 as an I/O device. The optical signal interface 126 may include control circuitry to activate one or more LEDs 130 to an on-state for an on-period of time. During the same on-period, control circuitry on the optical signal interface 126 receives a signal of electrical current corresponding to a light intensity value from a selected photodetector 120. The optical signal interface 126 may select the LEDs to activate, trigger the activation of LEDs 130, and select a photodetector to receive an input from using a clock signal and timing circuitry configured to control selecting circuitry. In an example implementation, the selecting circuitry may include an LED controller 134 configured to control a de-multiplexing array 138 by selecting de-multiplexers through which to output a power signal to activate the selected LEDs for the required on-period. During the same on-period, a photodetector controller 136 selects a path to receive the signal of current from the photodetector connected to the selected path.

The processor 124 through program control may select the LEDs and photodetectors through a sequence of on-periods until current signals are received from each of the C photodetectors corresponding to optical paths created between each photodetector and each of the R×C LEDs. Intensities may be measured for each optical path corresponding to the C photodetectors and the R×C LEDs during a sequence of R×C on-periods. The sequence of R×C on-periods may be repeated over a larger period of time to collect raw intensities corresponding to each optical path over a period of time sufficient to cover at least one heart beat. In addition, the raw intensities may be collected continuously while a connection between the patch 102 and the PPG data processing system 106 (or data relay 104) is in operation. The intensity values change according to the volumetric flow through the blood vessel, which changes in response to the cardiac cycle of the heartbeat.

The raw intensity values are received by the PPG data processing system 106 and processed to interpret the data and derive the desired metrics. Further processing of the intensity values is described above with reference to FIGS. 5A-5B and 6A-6C.

Figure 2C:
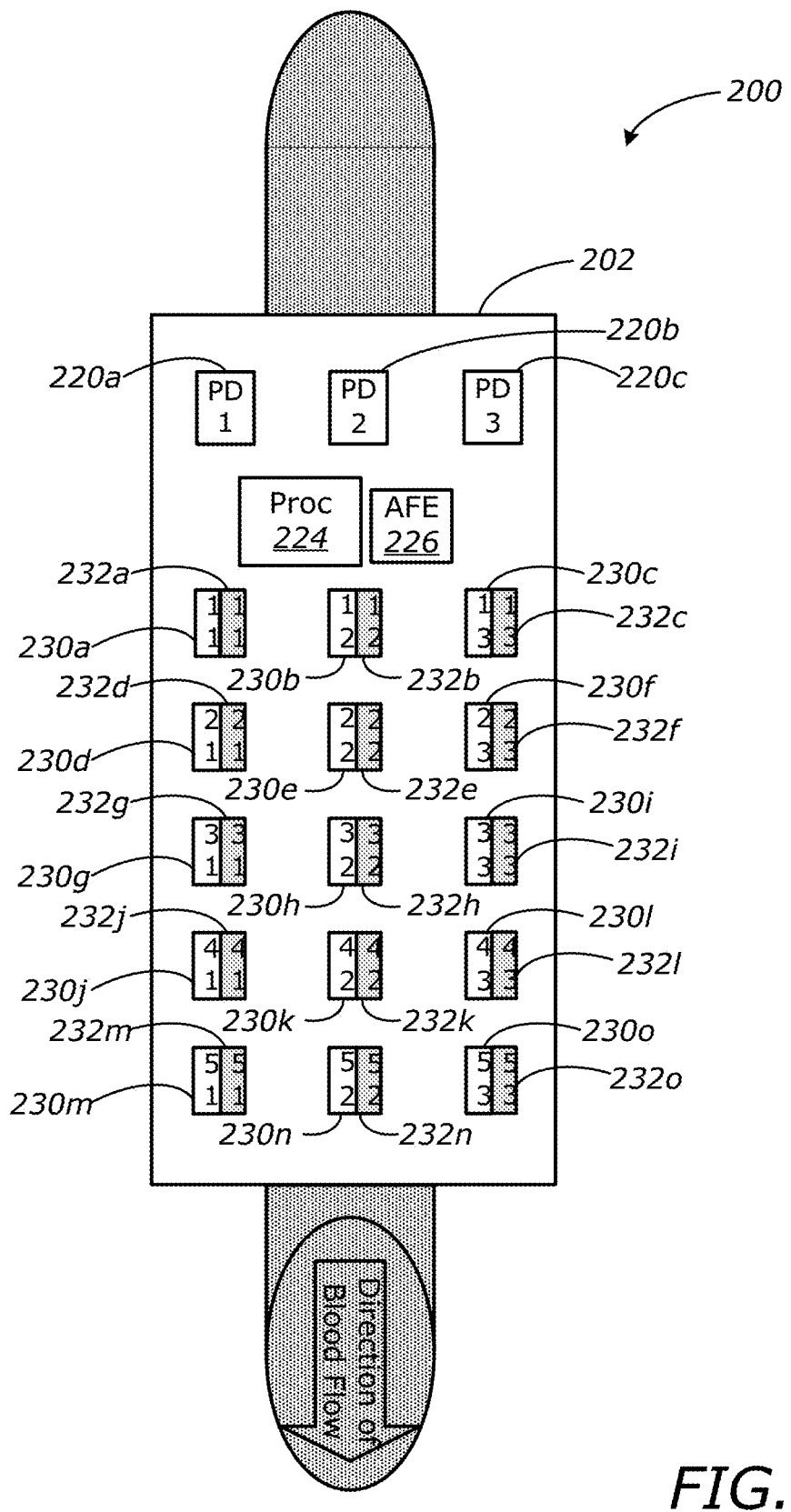
FIG. 2C is another example implementation of a patch configured to generate a plurality of optical paths for measuring biological metrics.

FIG. 2C is a schematic diagram of another example implementation of a patch 200 formed on a substrate 212 and configured to generate a plurality of optical paths for measuring biological metrics. The patch 200 in FIG. 2D is configured to determine biological metrics that may involve more than one wavelength. In an example implementation, the example patch 102 in FIG. 2A may be configured to operate using LEDs that emit IR light to measure hematocrit concentration and any other metric that may be determined from tissue interaction with IR light. The patch 200 in FIG. 2C may include a plurality of IR LEDs 230a-o and a plurality of red LEDs 232a-o each adjacent to a corresponding one of the IR LEDs. The red LEDs 232a-o and the IR LEDs 230a-o are preferably sufficiently close to each other so that the red LEDs may be deemed co-located with the IR LEDs so as to generate substantially converging optical paths at different wavelengths.

The patch 200 also includes C photodetectors 220 configured to receive the IR and the red light from the R×C IR LEDs and the R×C red LEDs. In an alternative implementation, the patch 200 may include C IR photodetectors configured to receive primarily the IR light from the IR LEDs and C red photodetectors configured to receive primarily the red light from the red LEDs. The patch 200 in FIG. 2C may be configured as described in this disclosure to determine Hct concentration using IR optical paths from the IR LEDs 230 and to determine SpO2 using IR optical paths from the IR LEDs and red optical paths from the red LEDs 232.

The patch 200 includes a processor 224, an optical signal interface 226, a memory (not shown), and a communications interface (not shown). The optical signal interface 226 may be configured to receive raw intensity values from IR optical paths generated by the PD-IR LED pairs and from red optical paths generated by the PD-red LED pairs. The optical signal interface 226 may operate using an on-period for each optical path as described above for the PD-LED optical paths generated for the patch 102 described above with reference to FIGS. 2A and 2B.

Figure 3:
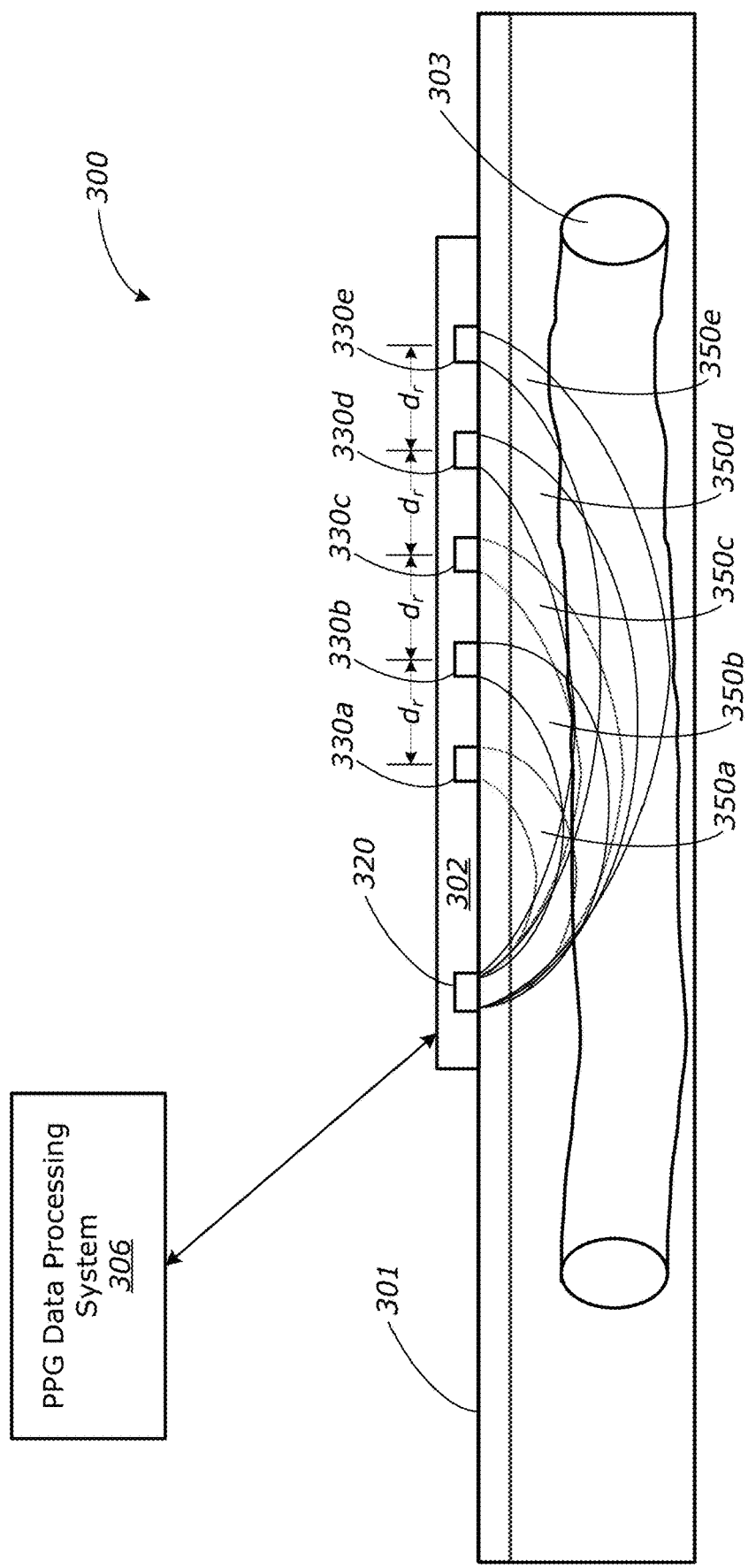
FIG. 3 is a schematic side cross-sectional view of an example of a patch over a blood vessel and generating a plurality of optical paths.

FIG. 3 is a schematic side cross-sectional view of an example of a patch 302 over a blood vessel 303 and generating a plurality of optical paths 350. The patch 302 is depicted in cross-section to show a photodetector 320 aligned along a column with five LEDs 330a-e disposed at substantially the same distance, dr, apart. The patch 302 is shown applied to the skin 301 above the blood vessel 303. When each LED 330 is activated, the LED 320 forms an optical path 350 with the photodetector 320.

Each optical path is illustrated as the light emitted from each LED 350 and received by the photodetectors 320. Light emitted by each LED 350 may be distributed from the LEDs in a substantially omni-directional pattern, or in a pattern substantially directed towards the photodetectors 320. The optical paths 350 are depicted in a substantially banana-shaped pattern as the light that reaches the photodetectors 320 and not the light dispersed in other directions. As shown in FIG. 3, optical path 350a is formed when LED 330a emits light through the tissue under the skin to be received by the photodetector 320. The optical path 350b is formed when LED 330b emits light through the tissue under the skin to be received by the photodetector 320. The optical path 350c is formed when LED 330c emits light through the tissue under the skin to be received by the photodetector 320. The optical path 350d is formed when LED 330d emits light through the tissue under the skin to be received by the photodetector 320. The optical path 350e is formed when LED 330e emits light through the tissue under the skin to be received by the photodetector 320.

It is noted that each optical path 350 in FIG. 3 may be illuminated sequentially and one optical path at a time so that the intensity readings read at the photodetector 320 corresponds to individual optical paths. The sequence of optical paths 350 are interrogated along a given column of LEDs 330a-e. Each column of LEDs may be referred to as a channel of optical paths.

The example in FIG. 3 depicts the patch 302 with five rows of LEDs 330a-e. In example implementations, the optical path 350a generated the LED 330a and the photodetector 320 may have a higher intensity than the optical paths from the LEDs 330b-e positioned further from the photodetector. The depth to which the optical path 350a extends is also the shallowest of the five optical paths 350. The optical path 350e between the photodetector 320 and the furthest LED 330e extends the deepest into and to some extent beneath the blood vessel 303. The most accurate readings may be obtained from optical paths that most overlap with the blood vessel. For a given implementation, an R×C matrix of LEDs and C photodetectors may be provided to interrogate blood vessels of different cross-sectional areas. Smaller blood vessels may be interrogated with a subset of the R×C optical paths. In addition, a larger matrix of LEDs and photodetectors may be disposed on the patch to interrogate larger blood vessels but configured to use subsets of the larger matrix to interrogate smaller blood vessels.

It is noted that in some implementations, the channel of optical paths may include LEDs in other columns forming optical paths with a given photodetector. In the implementations described herein, the channel of optical paths comprise the LEDs in a given column aligned with a given photodetector.

Figure 4A:
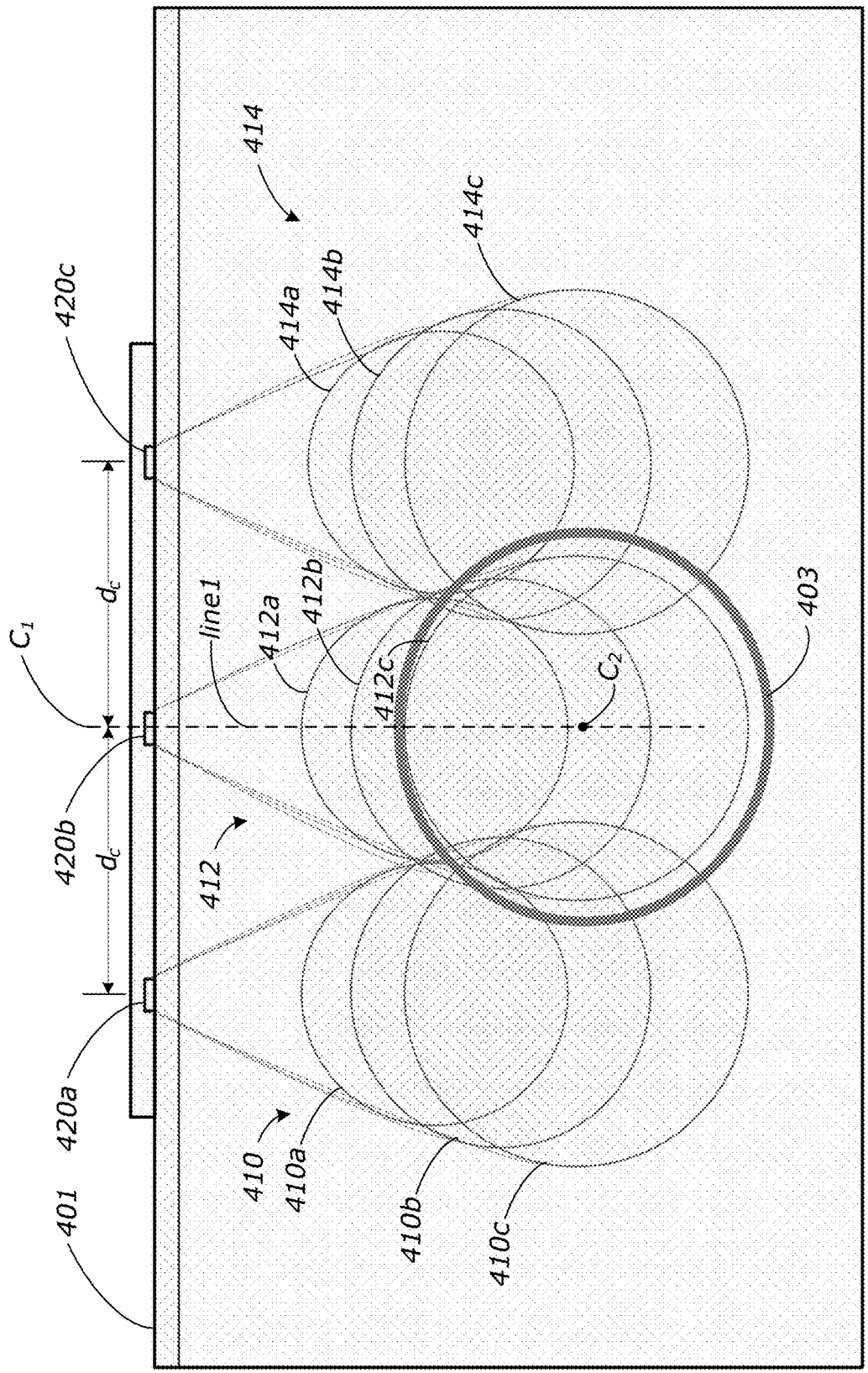
FIG. 4A is a front cross-sectional view of an example of a patch substantially centered over a blood vessel generating a plurality of optical paths.

FIG. 4A is a schematic front cross-sectional view of an example of a patch 402 substantially centered over a blood vessel 403 generating a plurality of optical paths 410a-c, 412a-c, and 414a-c. The cross-sectional view depicts three photodetectors spaced substantially the same distance, de, apart receiving the light from the optical paths from the LEDs (not shown). FIG. 4A depicts the optical paths 410a-c, 412a-c, and 414a-c from the front view of the cross-section of the blood vessel. The optical paths 410a-c, 412a-c, 414a-c form channels 410, 412, 414 as substantially round cross-sections having an overlap with the cross-section of the blood vessel 403. The optical paths 410, 412, 414 are formed by light emitted from the LEDs that is sensed by the photodetectors, and not light directed elsewhere. The channel having a cross-section that overlaps most with the cross-section of the blood vessel 403 represents signal paths that interact most with the blood flowing in the blood vessel 403. Such optical paths may provide the most accurate measurements from which to determine any biological metrics from the blood.

Figure 4B:
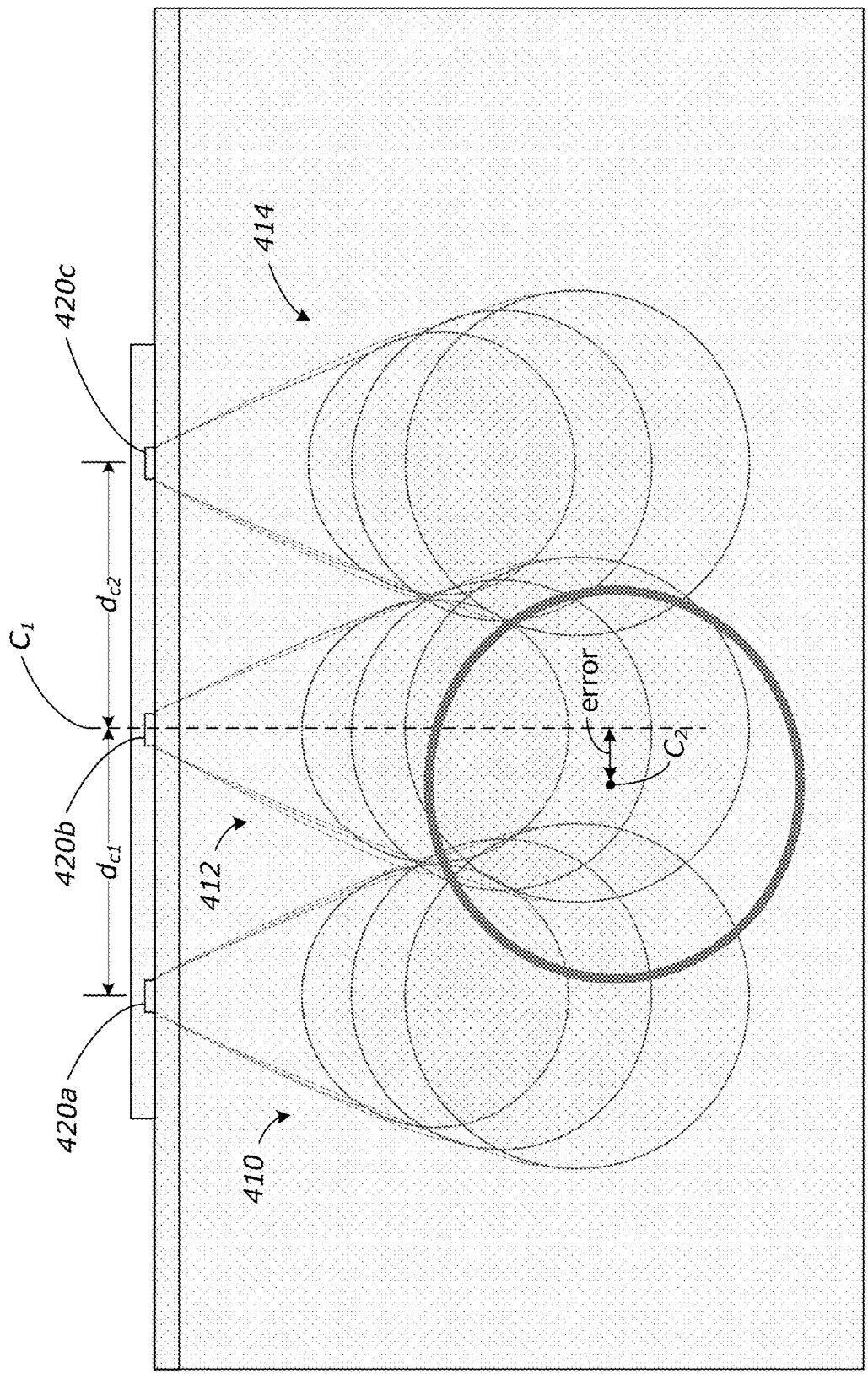
FIG. 4B is a front cross-sectional view of an example of a patch over a blood vessel generating a plurality of optical paths where the center of the patch is shifted from the center of the blood vessel.

During use, the patch 402 may be placed on the skin by medical personnel prior to configuring the system to collect optical data from the patch 402. The objective of the placement of the patch 402 is to ensure that a majority of the cross-sectional area of most of the channels overlap the cross-section of the blood vessel 403. Typically, this optimal placement is achieved when the center, $c_1$, of a length between the two outermost photodetectors aligns with the center, $c_2$, of the blood vessel along a line, $l_2$, perpendicular to a line between the two outermost photodetectors. An optimal placement is not always possible and the patch 402 may often be placed such that the center, $c_2$, of the blood vessel is offset by an error distance as shown in FIG. 4B. Further analysis described below may be performed to determine the best optical path or optical paths from which to obtain the metric measure regardless of an offset from an alignment between the center of the blood vessel and the center of the row of photodetectors.

Figure 5A:
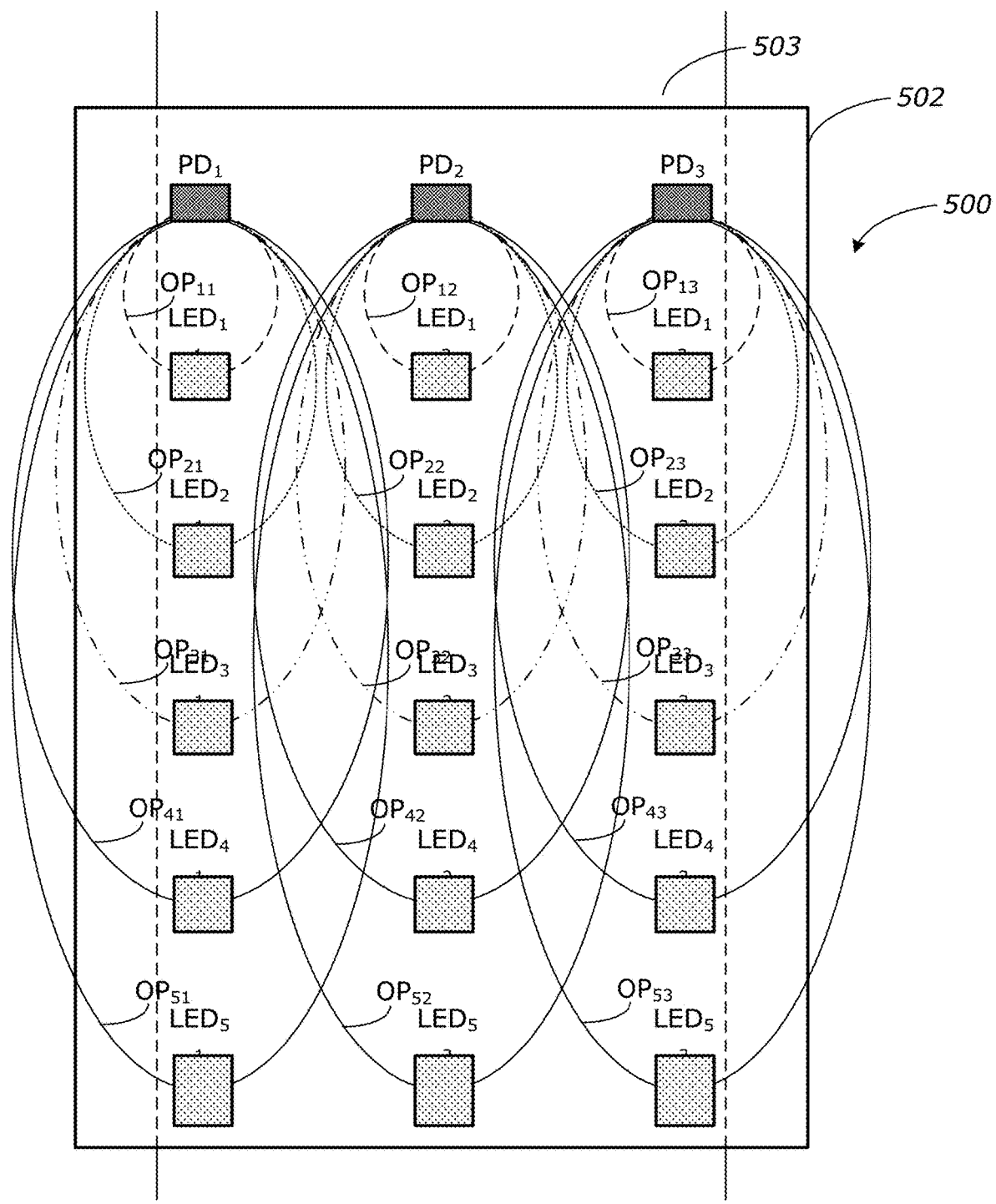
FIG. 5A is a schematic top view of an example of a plurality of optical paths formed on an example patch.

FIG. 5A is a top schematic view of an example of a patch 502 having a plurality of optical paths $OP_{rc}$ between R=5 by C=3 (15) LEDs ($LED_{rc}$) and C=3 photodetectors (PD). The patch 502 is positioned over a blood vessel 501 to interrogate the blood vessel 501 for, in this example, hematocrit concentration (Hct).

In an example implementation, the optical paths $OP_{rc}$ are formed by the activation of one of the LEDs, $LED_{rc}$, and the input to the photodetector PDrc in the same column as the $LED_{rc}$. While the optical paths $OP_{rc}$ are depicted in FIG. 5B in an On-state, the optical paths may be formed, or turned ON, one at a time during on-periods during a period of time.

Figure 5B:
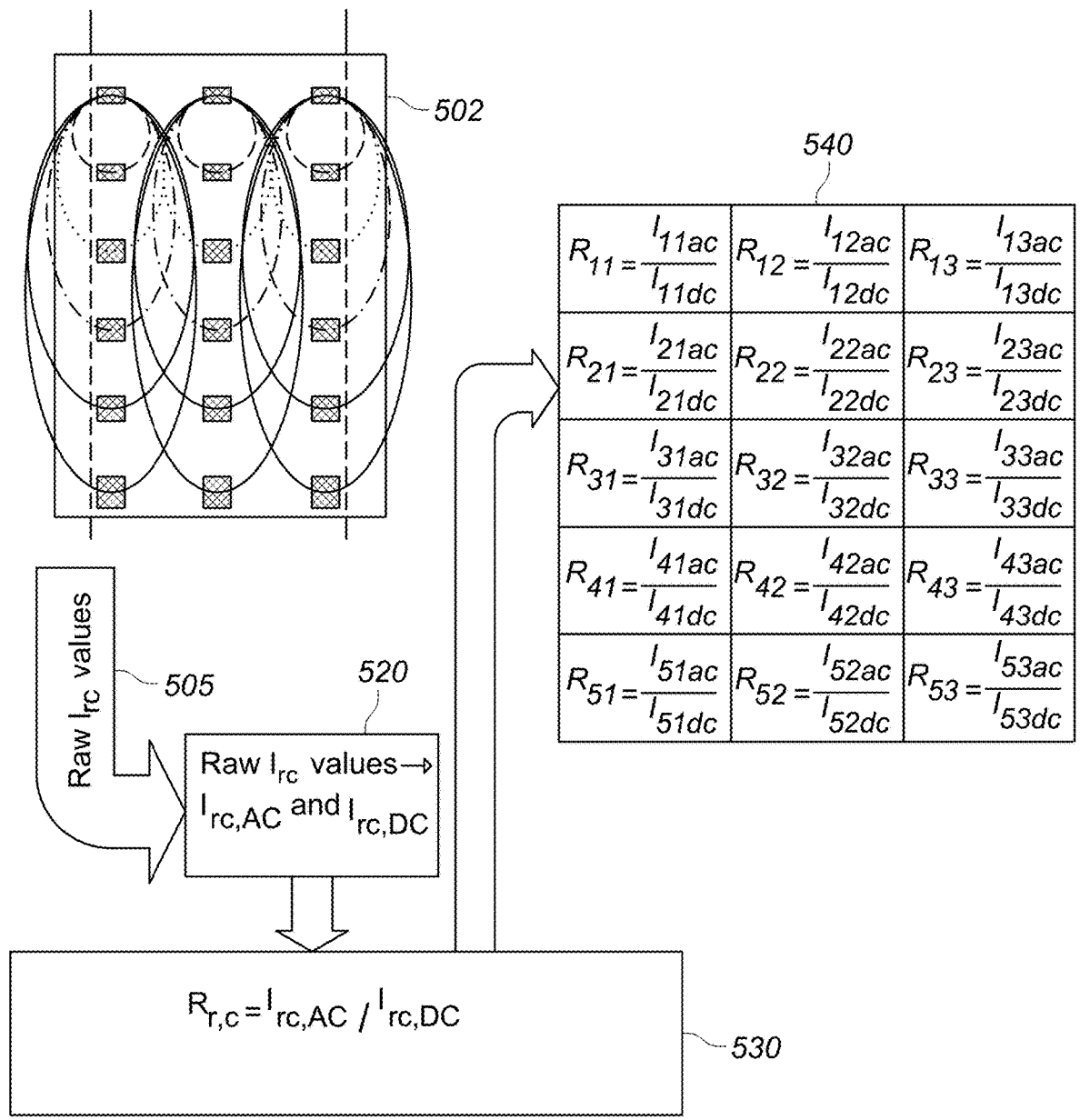
FIG. 5B is a flow diagram illustrating an example of a determination of AC-to-DC ratios for the plurality of optical paths in FIG. 5A.

Referring to FIG. 5B, as each optical path $OP_{rc}$ is formed, the patch 502 receives raw intensity signals at 505 via the photodetector, PDc. The raw intensity signals may be further processed using signal processing techniques to eliminate noise, provide compression, perform filtering or other signal processing techniques. The raw intensity values are then used to calculate an AC and a DC component at 520.

The AC component may be determined using: $I_{rc,AC} = f(I_{rc})$, where $f(I_{mr})$ is a first or higher order bandpass filter, which may be determined experimentally for a specific implementation. An example implementation may use a finite impulse response (FIR) bandpass filter to process the PPG signal. The particular parameters of the FIR filter may be adjusted based on the detected heart rate of each data recording, so as to preserve the same waveform features regardless of the patient's heart rate, which can vary by a factor of three even in healthy subjects. This processed waveform can be analyzed using an autocorrelation algorithm to identify individual heartbeat waveforms. The AC component of the waveform can be computed as the mean amplitude of these heartbeat waveforms.

The DC component may be determined using:

$$I_{rc,DC} = \text{mean of } I_{rc} : \frac{1}{n}\sum_{i=1}^{n} I_{rc_i}$$

for n samples collected over a time period. The AC and DC components may be calculated for intensity values from each optical path over the time period, which may be sufficiently long to encompass at least one heartbeat. The time period may constitute a cycle that can be repeated for any desired amount of time. In an example implementation, the patch 502 includes an accelerometer, which communicates signals indicative of motion of the patent wearing the patch 502. The motion signals may be compared on a timeline with the AC and DC components to identify any AC and DC components whose values may be affected by the motion. The AC and DC components affected by motion may be discarded or otherwise processed accordingly.

Once the AC and DC components are determined at 520, a ratio of the AC to DC components, Rrc, is determined at 530 for each optical path. The AC to DC component ratios are shown in FIG. 5B at 540 as a matrix corresponding to the R×C matrix of LEDs. Each column corresponds to the columns associated with each photodetector. The top row of AC to DC component ratios corresponds to the optical paths formed by the row of LEDs closest to the row of photodetectors.

Once a plurality of AC to DC component ratios are determined as shown in the matrix 540 in FIG. 5B, the AC to DC component ratios may be further divided with one another, or with a reference AC to DC component ratio to provide a framework in which to further analyze the signals received via the optical paths. FIG. 5C illustrates alternative RoR formulations that may be used in the further analysis. At 550 in FIG. 5C, the AC to DC component ratios of each row in the matrix 540 in FIG. 5B are divided by the AC to DC component ratios of the first row of AC to DC component ratios in the matrix 540 in FIG. 5B. At 560 in FIG. 5C. the AC to DC component ratios of the optical path corresponding to each nearer LED is divided by the AC to DC component ratio of the optical path corresponding to the next further LED after the first row corresponding to the optical paths corresponding to the nearest LEDs. The RoRs determined for the optical paths corresponding to the nearest LEDs are the AC to DC component ratios divided by themselves resulting in a value of 1, or 100% for each.

The matrices 550 and 560 in FIG. 5C are only two examples of how RoRs may be determined. Other ways of determining RoRs may be implemented, and optimal ways of determining RoRs may depend on the size of the grid (number of rows and columns), the distance between components ($d_r$ and $d_c$), the approximate size of the blood vessel being interrogated, the wavelengths of the LEDs in the PPG grid, and other factors.

Figure 6:
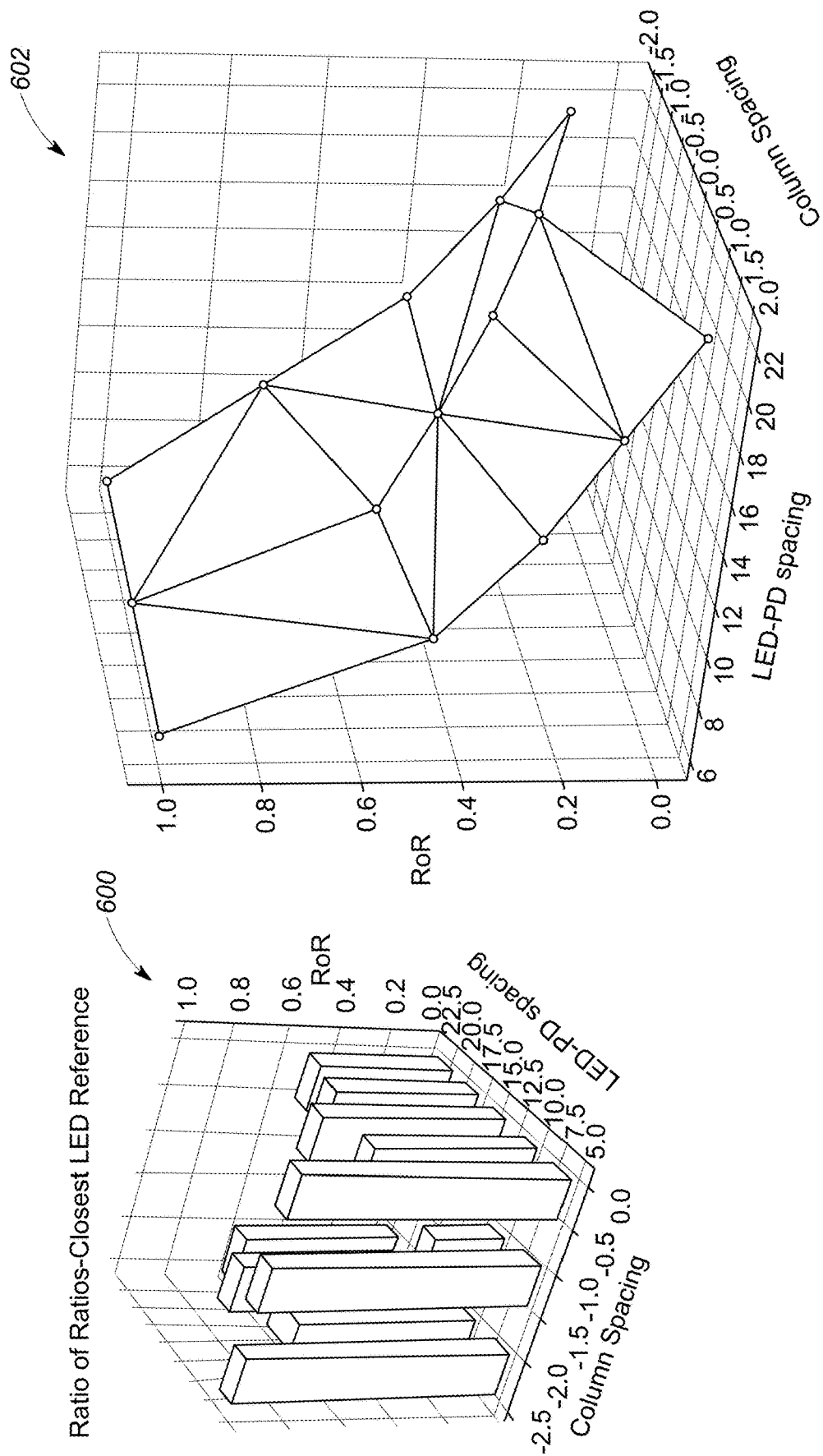
FIG. 6 are examples of graphs of RoR values plotted against the LED locations relative to the photodetectors in an example PPG grid.

In example implementations, an array of RoRs may be determined for use in a transfer function as described above. A transfer function may be derived from reference RoRs measured from a blood vessel having known blood metrics using regression analysis techniques. FIG. 6 depicts two plots of RoR values corresponding to LED and photodetector positions on an example PPG grid.

Referring to FIG. 6, a first plot 600 depicts RoR values on a vertical axis plotted to correspond with the LED position on a two-dimensional plane. The two-dimensional plane has a column spacing on one axis and an LED to photodetector (PD) spacing on the other axis. In the first plot 600, the row of LEDs closest to the row of photodetectors is selected as a reference. The RoR values plotted in the first plot 600 may be determined, for example, using the method of determining RoRs illustrated above in matrix 550 in FIG. 5C.

The data corresponding to the first plot 600 may be analyzed to select a subset of RoRs to use in a transfer function configured for that subset of RoRs. For example, a transfer function may be configured to determine a blood metric, Hct concentration, for example, based on the RoRs in a column of RoRs determined to be an optimal column. Based on the example illustrated in the first plot 600, the transfer function would be configured to use up to five RoR values in the optimum column. In other implementations, a transfer function may have different numbers of RoR values as inputs depending on the size (R×C) of the matrix of LEDs and photodetectors and the level of complexity desired for the implementation.

The RoR values may also be analyzed to determine optimality. For example, the RoR values determined using techniques described above with reference to FIG. 5B may be analyzed to determine the best optical path or optical paths to use for determining an Hct. In one example implementation, the maximum value of the RoR values may be deemed to correspond to the best column of optical paths for determining the Hct. In another example, the RoR values may be used to determine an optimum optical path from which to select an AC to DC component ratio to use in the transfer function. In such an example, the optimum optical path may correspond to the optical path having the highest RoR value.

The transfer function may also be configured to use all RoR values for the PPG grid. The RoR values may be used in the transfer function as discrete values, for example. The transfer function may also correspond to a surface fitting of the RoR value set. A second plot 602 in FIG. 6 depicts the RoR values plotted as a surface relative to LED positions and photodetectors on an example PPG grid. The second plot 602 illustrates a data model that may entail a transfer function that fits a surface defined by the RoR values to a surface defined by reference data. The transfer function could therefore take as inputs the coefficients defining this surface—rather than the entire set of RoR values—reducing the complexity of the transfer function. The transfer function that may be used with the RoR values may be selected depending on the complexity of the calculations, performance measured against a reference measurement system, the possibility of using quality weighting of measured data, and the ease with which the selected technique can be adapted to different PPG grids.

The description above with reference to FIGS. 5A, 5B and 6 illustrates the calculation and use of RoR values derived from optical measurements taken by a PPG grid having multiple light sources and photodetectors where light is emitted at a single wavelength. In measuring Hct, the wavelength may be in the IR region of the spectrum since the IR signals are a function of the interaction of the IR light with the hemoglobin in red blood cells. Other blood metrics may be determined based on the interaction of tissue with light in other wavelengths. Light at multiple wavelengths may be measured for other blood metrics.

Figure 7A:
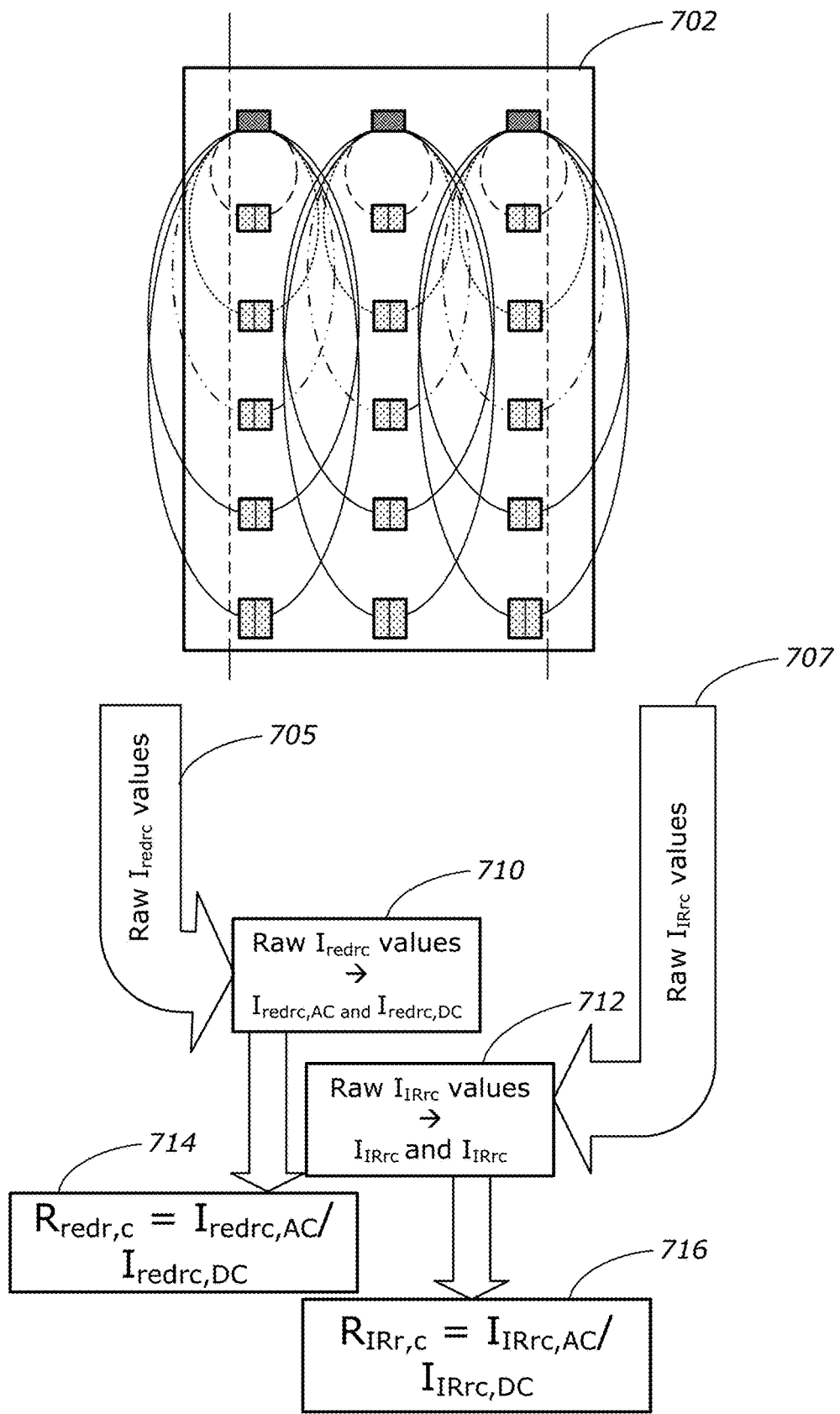
FIG. 7A is a schematic top view of another example of a plurality of optical paths formed at two wavelengths on an example patch and a flow diagram illustrating operation of another example method for determining AC-to-DC components ratios at two different wavelengths.
Figure 7B:
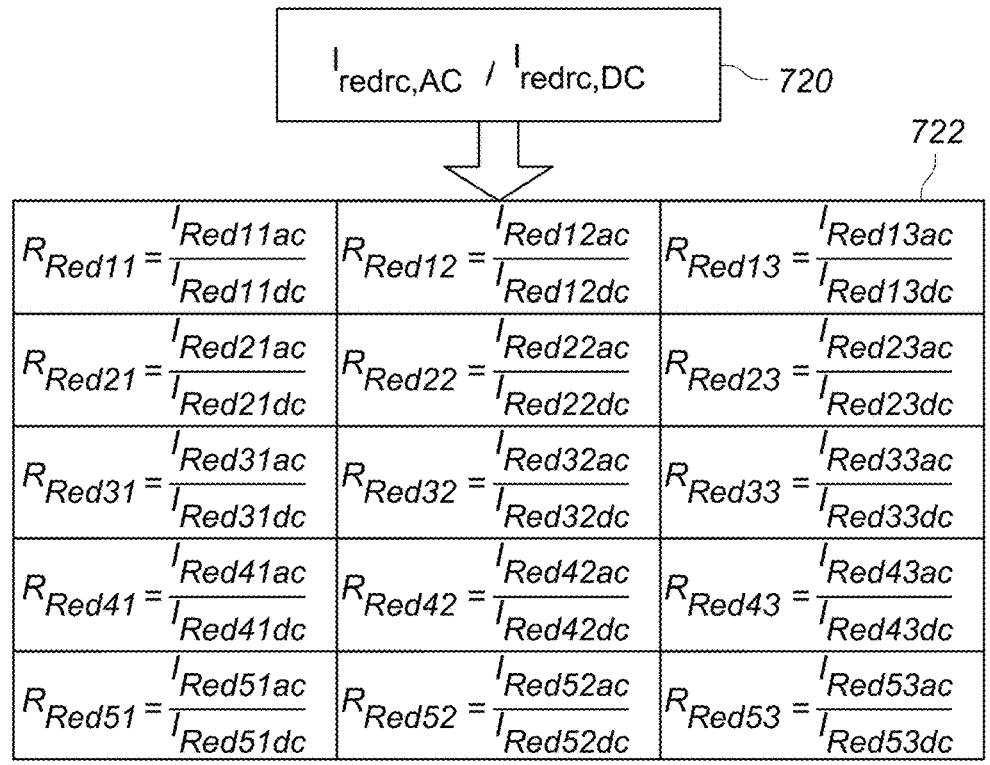
Figure 7B:
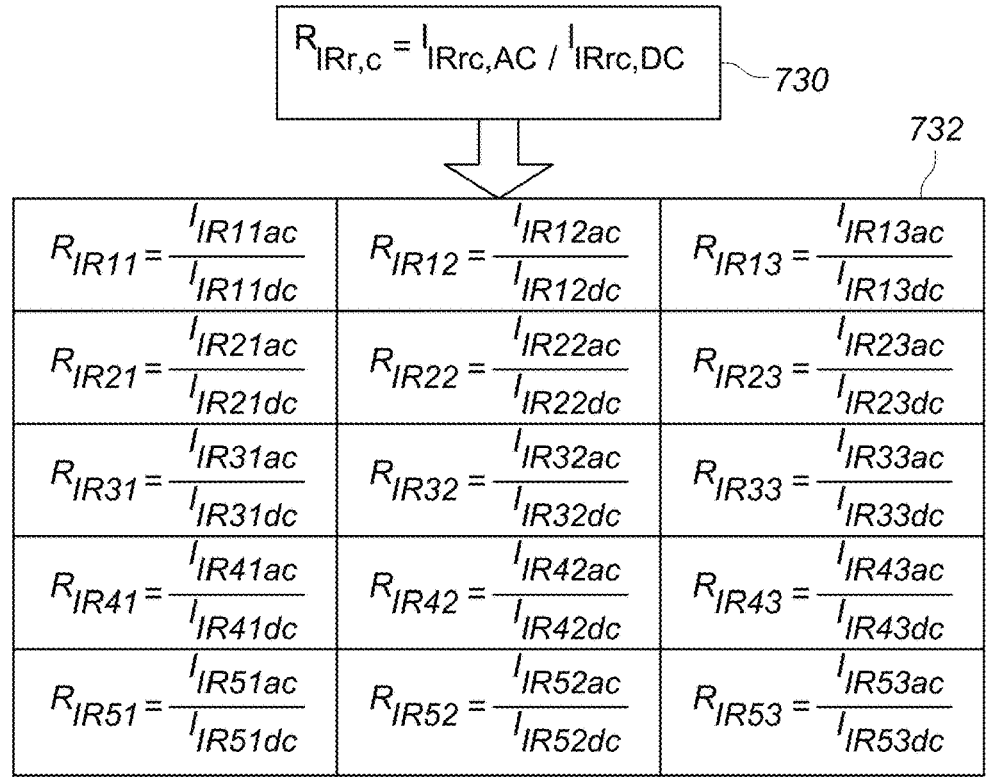

The analytical approach described above may be incorporated for other blood metrics using more than one wavelength. For example, a ratio-of-ratio analysis may be used from light measured in two wavelengths to determine blood metrics, such as for example, SpO2. FIG. 7A is a schematic top view of another example of a plurality of optical paths formed at two wavelengths on an example patch and a flow diagram illustrating operation of another example method for determining AC to DC components ratios at two different wavelengths. FIGS. 7B-7D are flow diagrams and matrices illustrating examples of methods for determining ratios of ratios for the plurality of optical paths at two wavelengths. The examples described with reference to FIGS. 7A to 7D may be used in determining, for example, SpO2.

As shown in FIG. 7A, a patch 702 may include a row of photodetectors and a plurality of rows of LED pairs extending in columns from each photodetector, which each LED pair includes an IR LED and a red LED. The patch 702 may be an example of the patch 202 in FIG. 2C. Raw intensity values 705 from the red LEDs and raw intensity values 707 from the IR LEDs may be received at on-periods during time periods spanning at least one cardiac cycle in a manner similar to that described above with reference to FIGS. 5A-5B. The red intensity values 705 from each optical path corresponding to each red LED may be used to calculate red AC components and red DC components at 710. The IR intensity values 707 from each optical path corresponding to each IR LED may be used to calculate IR AC components and IR DC components at 712. The AC and DC components may be calculated in a manner similar to that described above with reference to FIG. 5A. At 714, a red AC to DC component ratio may be determined from the AC and DC values for optical paths corresponding to each of the red LEDs. At 716, an IR AC to DC component ratio may be determined from the IR AC and DC values for optical paths corresponding to each of the IR LEDs.

Referring to FIG. 7B, the red AC to DC component ratios at 720 may be determined for each red optical path to derive a set of ratios at 722. The IR AC to DC component ratios at 730 may be determined for each red optical path to derive a set of ratios at 732. Referring to FIG. 7C, the red AC to DC component ratios 721 and the IR AC to DC component ratios 731 may be divided to obtain composite RoRs as shown in 740. The composite RoRs at 740 are ratios of AC to DC component ratios for red divided by AC to DC component ratios for IR LEDs.

The composite RoRs may be used to determine RoR values for analysis. The composite RoRs of the first row of composite RoRs may be used as a reference by dividing the first row of composite RoRs by themselves, and each row of composite RoRs corresponding to each LED pair positioned further from the photodetector may be divided by the composite RoRs in the first row as shown in 750. Referring to FIG. 7D, another example set of RoR values may be determined by using the first row of composite RoRs as a reference as described above, and dividing each further row of composite RoRs by the next nearer row of composite RoRs as shown at 760. The RoRs in 750 or 760 may then be used for analysis to select RoR values to use in a transfer function in a manner similar to that described above with reference to FIGS. 5A and 5B.

The ratio-of-ratio analysis described above with reference to FIGS. 5A-5C, 6, and 7A-7D advantageously allows for a more accurate determination of biological metrics such as Hct and SpO2. In example implementations, the ratio-of-ratio analysis may also be used to determine information relating to geometric properties of the blood vessel being interrogated.

Example implementations of systems and methods for determining blood metrics by analyzing optical signals received from a matrix of LEDs and photodetectors disposed on a patch attached to a patient over a blood vessel are described above with reference to FIGS. 1-7A and 7B. Optical measurements received at the photodetectors are used to generate matrices of AC-to-DC component ratios corresponding to the optical paths formed by the LEDs and photodetectors in the matrix. A ratio-of-ratios analysis may be curve fit to a transfer function for providing blood metrics such as HCT, SpO2, etc. The transfer functions may be constructed, as described above, by positioning the matrix of LEDs and photodetectors over a blood vessel to perform the analysis where the blood metric levels are known. The transfer function may then be used to determine the blood metrics based on a ratio-of-ratios analysis from optical measurements received from the LED and photodetector matrix on the patch.

Figure 8A:
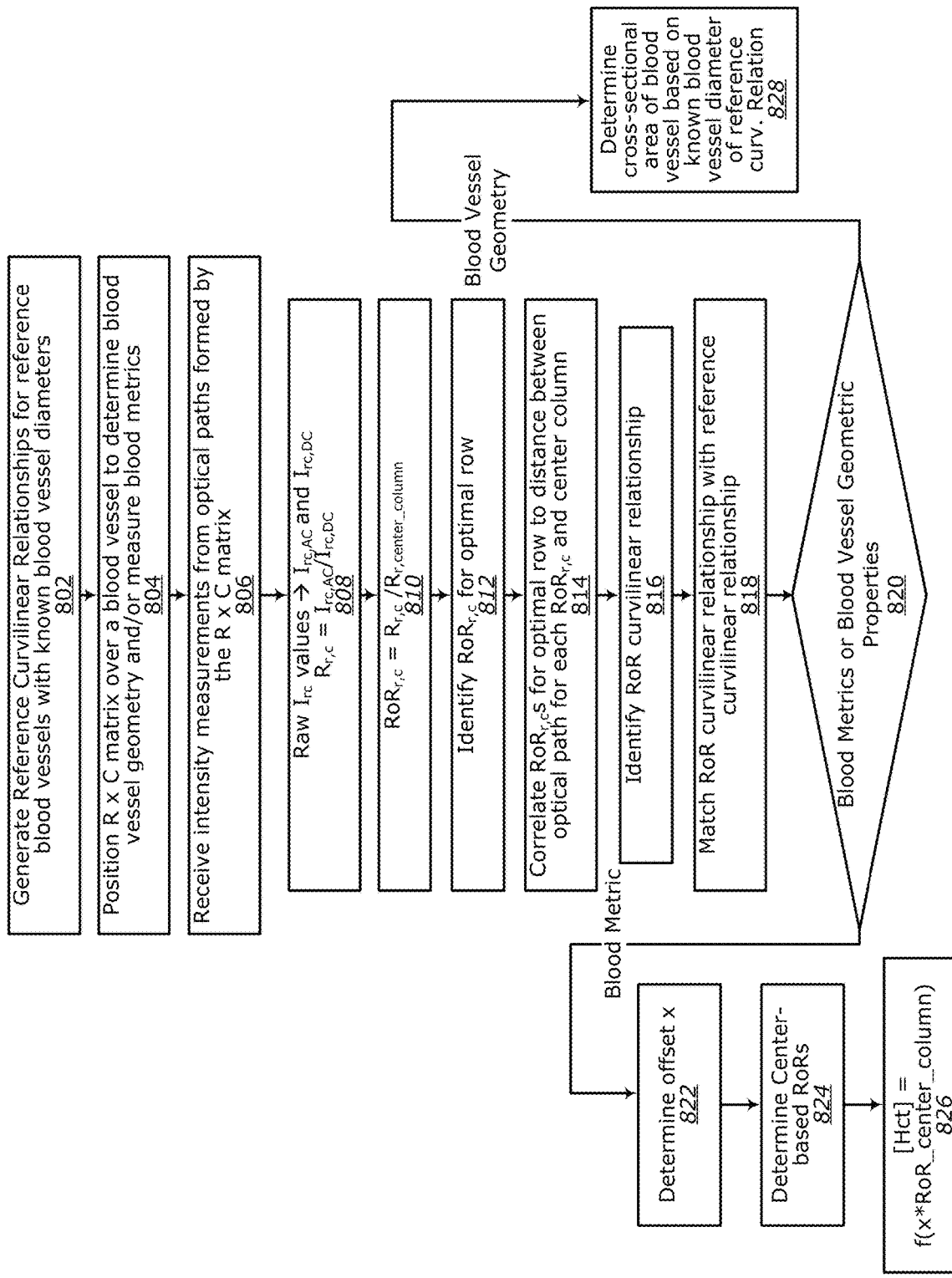
FIG. 8A is a flowchart illustrating operation of an example of a method for generating reference curvilinear relationships to determine geometric properties of a blood vessel or to measure blood metrics for blood flow in a blood vessel.

Example implementations of the matrix of LEDs and photodetectors may also be used for ratio-of-ratios analysis across rows to obtain information relating to geometric properties of blood vessels as well as for more accurate blood metrics. FIG. 8A is a flowchart illustrating operation of an example of a method for generating reference curvilinear relationships and analyzing sets of ratio-of-ratios against the reference curvilinear relationships to determine geometric properties of a blood vessel. In an example implementation, an analysis of ratio-of-ratios sets may also be used to measure blood metrics of blood flow in a blood vessel.

The generation of reference curvilinear relationships may be performed as a calibration or configuration step for the patch 102 (in FIG. 1). The reference curvilinear relationships provide options for curve-fitting ratio-of-ratios data for optical measurements received when interrogating blood vessels of different sizes. The accuracy of the measurement of blood metrics is enhanced by ensuring that the results correspond to a higher degree of interaction between signal and blood tissue.

At step 802 in FIG. 8A, a plurality of reference curvilinear relationships may be generated for a patch 102 (FIG. 1). The step may be performed before deployment as a configuration step for a batch of patches or a single patch. In an example implementation, the patch may be configured by collecting optical measurements from multiple blood vessels each having different sized blood vessels. During configuration, the patch may be positioned with a center column of the matrix of LEDs and photodetectors directly over an imaginary line running through the center of the cross-sectional area of the blood vessel. The centering of the patch over the blood vessel, and the determination of the diameter of the blood vessel, for example, may be accomplished using imaging techniques during or substantially contemporaneously with the collection of optical data. The optical measurements for generating the reference curvilinear relationships may be performed using any suitable configuration.

As noted above, the reference curvilinear relationships allow for the processing of the optical measurements as primarily an interaction between photons and blood. Referring to FIG. 3, the IR signals in the optical paths 350 are primarily a function of the interaction of the IR energy with the hemoglobin in the red blood cells. In proximity to the blood vessel, the resulting signal of each optical channel is a function of the overlap of the optical path and the cross sectional area of the blood vessel. This relationship can be expressed as:

$k_{rc}R_{rc}$, where:

$k_{rc}$ is a scaling constant for the optical path between photodetector $PD_c$ and $LED_{rc}$.

$R_{rc}$ The AC/DC ratio of $PD_c$ and $LED_{rc}$.

The scaling constant for each optical path in the context of determining vessel geometry is intended to normalize the channel response for differences in intensity due to geometry and depth. The geometry and depth of the vessel can be approximated by taking slices of the cross-sectional area of the vessel moving from outside the vessel radius. The ratio-of-ratios for each optical channel should have a magnitude corresponding to the amount of overlap between the optical channel and the blood vessel. If the optical channel entirely overlaps the blood vessel, the magnitude of the ratio-of-ratios for that optical channel approaches a peak value for the ratio-of-ratios. As the optical channel crosses the area of the blood vessel, less of the optical channel overlaps the blood vessel. Using this relationship and calculating expected ratio-of-ratios for optical channels as the vessel width varies relative to the spacing of the collinear channels (i.e., traversing across the vessel), a plurality of curves can be generated as described below with reference to FIG. 8B.

Figure 8B:
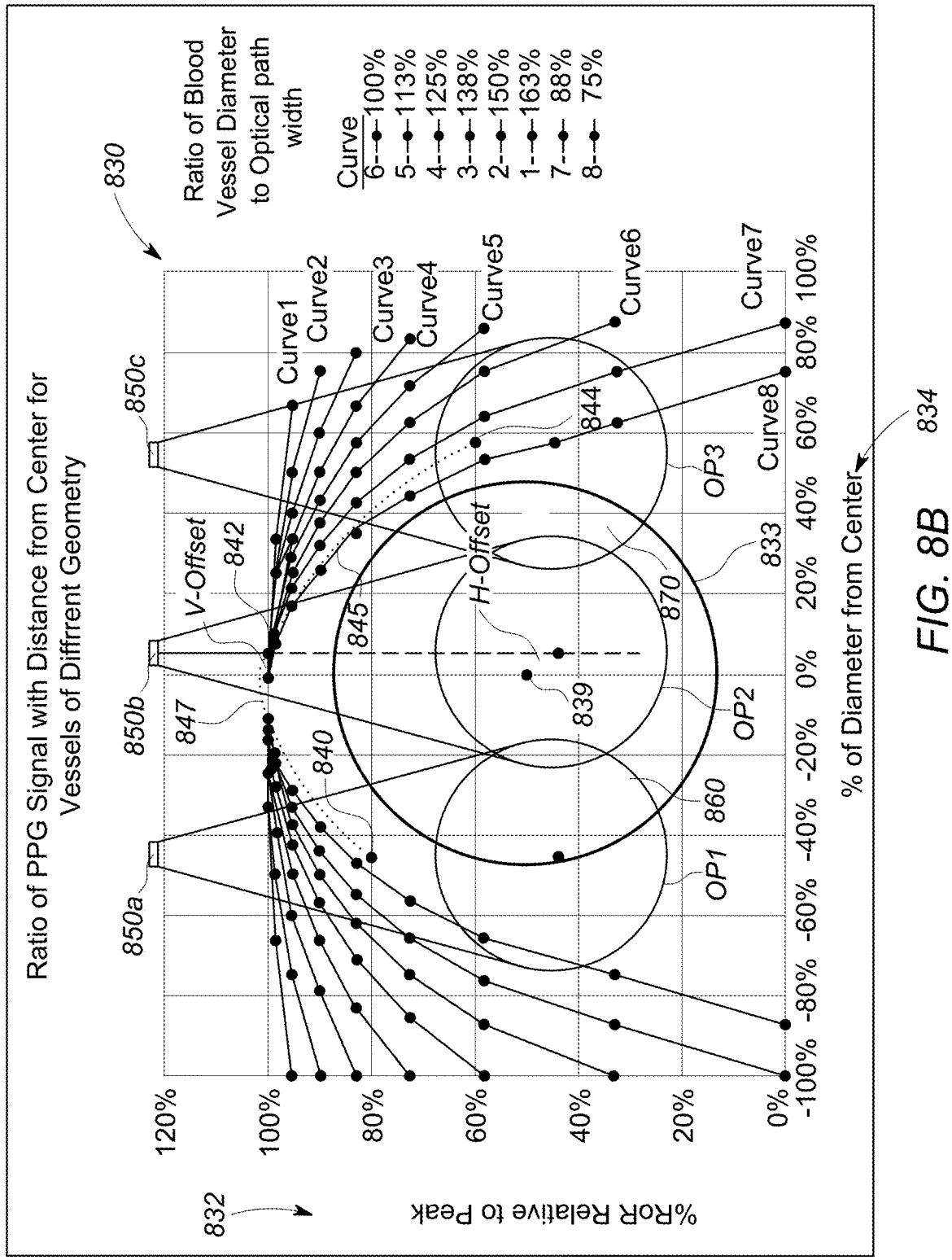
FIG. 8B is an example of graphs of a plurality of curves illustrating a curvilinear relationship between a percent of ratio-of-ratios relative to a peak ratio-of-ratios and a channel distance to a channel center in terms of percent of radius of the blood vessel and example plots of determined ratios of ratios for multiple channels of a patch.

The graph 830 in FIG. 8B depicts eight reference curvilinear relationships, or reference curves (curve1 to curve8) each corresponding to a different ratio of blood vessel diameter to optical width diameter. That is, each reference curve represents a correlation between the area of the optical path and the area of the blood vessel. Above the reference curves, three photodetectors 850a, 850b, and 850c indicate an endpoint of three optical paths OP1, OP2, OP3 superimposed over the graph. The photodetectors 850 are positioned at a distance $d_c$ (see FIGS. 4A and 4B) from each other. The distance $d_c$ corresponds to a distance between the photodetectors on the patch.

The graph 830 in FIG. 8B has a vertical axis corresponding to a percent RoR relative to a peak RoR value 832. The horizontal axis of the graph 830 in FIG. 8B is a percent diameter from the blood vessel center 834. The curves correlate the percent RoR values relative to peak with the location of the center of each optical path relative to a distance from the blood vessel center 834 based on a percent of diameter of the blood vessel.

The peak RoR value may be the RoR value calculated for measurements where the center column of the LED arrays aligns with the blood vessel such that the optical path for the center column overlap completely with the cross section of the blood vessel. The reference curves (curve1 to curve8) may be plotted from measurements taken from an array having a center column aligned with the blood vessel. The RoR values plotted for each curve may correspond to optical paths formed by LEDs in a row. The RoR values may be determined by dividing the AC-to-DC component ratio for each optical path in a row of LEDs by the AC-to-DC component ratio for the optical path formed by the LED from the center column in the given row.

It is noted that the graph 830 in FIG. 8B may be stored in memory as a data structure comprising data elements and relationships that correspond to the curves shown in FIG. 8B. Algorithms may be developed to process the optical measurements according to the description provided in this disclosure and incorporated in the system without resorting to plots of the graph. The algorithms, which may incorporate machine learning, lookup tables, and other technologies, may be implemented as software programs stored in memory as part of the system 100 (FIG. 1), for example, to process optical measurements from the patch 102 (FIG. 1) as described herein.

In generating the curves in FIG. 8B, optical measurements are received and processed optical paths as described above. The optical measurements are used to determine AC-to-DC components for each optical path. The optical paths for the LEDs in the center column ($R_{r2}$, for each row r=1-5) define the RoR values when the center column is aligned with the blood vessel. The AC-to-DC components for the optical paths in the center column are at the peak AC-to-DC component values. The percent RoR value relative to peak would be 100%. Accordingly, the percent RoR value relative to peak is 100% for each curve, curvet to curve 8, in FIG. 8B.

At step 804 in FIG. 8A, the patch 102 (in FIG. 1) now configured by construction of the reference curvilinear relationship as described above with reference to FIGS. 3 and 8B may be positioned over a blood vessel to determine blood vessel geometry and/or blood metrics. The optical measurements may be received as described above as intensity values, which may be used to determine AC-to-DC component ratios for each optical path as described above with reference to FIGS. 5A-5C. For example, at step 806, intensity measurements may be received for the optical paths formed by the R×C matrix of LEDs and photodetectors on the patch 102 (in FIG. 1). The raw intensity values may be used to determine AC components and DC components, and then ratios of AC-to-DC components at step 808.

The curves in graph 830 track the change in RoR values as the optical paths move away from the center of the blood vessel. The RoR value at the center of the blood vessel would be at its peak value. As the optical paths are positioned away from center, the RoR value decreases since less of the cross-section of the optical path intersects with the blood vessel. As shown in FIG. 8B, the optical paths OP1 and OP3 corresponding to the two outer photodetectors 850a and 850c only partially intersect the blood vessel 833 as indicated by areas 860 and 870. The first reference curve, curvet, corresponds to the largest blood vessel measured for the graph 800. As the optical paths move away from the center of the blood vessel, the RoR values decrease more slowly since the larger area of the blood vessel allows for the overlap of the optical paths to decrease at a slower rate. Curvet is therefore the flattest of the eight curves. In the illustrated example, curvet corresponds to a blood vessel having a diameter that is 163% of the optical path width. The second curve, curve2, and each subsequent curve drops off more quickly as the optical paths move away from the blood vessel center. The ratios of blood vessel diameters to optical path widths correspond to each curve as shown in the legend on the right of FIG. 8A.

At step 810, the AC-to-DC component ratios for the optical paths are used to calculate the table of RoRs across rows. In the description that follows, the optical measurements are processed to generate the set of RoRs as shown in the RoR table 880 in FIG. 8C. A table of AC to DC components similar to the table at 540 in FIG. 5A, which may be generated at step 808, may be processed to generate the RoR table 880 in FIG. 8C. The table 880 in FIG. 8C includes RoR values determined by dividing the AC to DC component ratios in the three columns of the optical path matrix (540 in FIG. 5B) by the AC to DC component ratios in the center column ($R_{r2}$ in 540 in FIG. 5B) as described above.

It is noted that at step 810, the table of RoRs 880 in FIG. 8C is a set of RoRs calculated across rows using the AC-to-DC component of the center column as the divisor. Alternatively, the table of AC-to-DC components may be divided by a peak reference value determined during configuration using known blood vessel diameters and blood metric values. Using the peak reference AC-to-DC component as a divisor results in an RoR table 890 in FIG. 8C.

At step 812 in FIG. 8A, the table 880 of RoR values in FIG. 8C may be analyzed to determine an optimal row, which may correspond to the row with the highest values. It is noted that alternatives to determining an optimal row may be used. For example, a weighted average of all rows may be determined for each column. The three weighted average RoR values may be used with the graph 830 in FIG. 8B.

The three RoR values may be plotted in the graph 830 in FIG. 8B. The points, shown in FIG. 8B as points 840, 842, and 814 correspond to the centers of each optical path OP1, OP2, OP3 located in alignment with the three photodetectors 820a-c. At step 814, the position of the three points may correlate with a distance between each optical path and the center column. At step 816, an RoR curvilinear relationship is identified for the three points. The three RoR values 840, 842, 844 may be fit to a curve 845 (the dashed line curve through values 840, 842, and 844) in a curvilinear relationship that may align or match with one of the reference curves (curve1 through curve 8) plotted in the graph 830. At step 818, the RoR curvilinear relationship may be matched to one of the reference curves.

It is noted that during implementation, the center RoR value 842 may not match with the curve peak corresponding to the center of the blood vessel 833. This would indicate that the photodetectors are not positioned so that the center point of the line between the outermost photodetectors is not aligned with the center of the blood vessel as shown at H-offset in FIG. 8C. A peak 847 of the curve 845 may be higher than the peak (at 100% RoR relative to peak) of the reference curves (curve1 to curve 8), which is designated in the graph 830 as a V-offset. Shifting the plotted points sideways and downward may align the curve 845 with one of the curves, or between two curves.

The curve with which the three points 840, 842, 844 align corresponds to a ratio of blood vessel diameter to optical path expressed as a percentage as shown in the legend in FIG. 8B. The alignment of the three points 840, 842, and 844 with the photodetectors 850 when the three points 840, 842, and 844 are shifted so the center column photodetector aligns with the center of the curve places the outer points 840 and 844 at a known distance, de (e.g., in FIG. 4), from the center of the blood vessel. This known distance, de (e.g., in FIG. 4), may be compared with where the outer points align with the horizontal axis, which is the percentage.

At decision block 820, the calculated data (RoR table 880 or 890) and the matching of the data with the reference curvilinear relationship from one of the curves may be used to either determine geometric properties of the blood vessel or calculate blood metrics.

Once the RoR points 840, 842, 844 are located on the horizontal axis, the optical path diameter may be determined. In addition, once the points 840, 842, and 844 are associated with one of the curves, the ratio of blood vessel diameter to optical path width may be used to determine a diameter of the blood vessel, which may be used to determine the cross-sectional area of the blood vessel.

At step 828, FIG. 8B illustrates using curves (curve1 to curve8) and the aligning of the curves with data that is curve-fit relative to RoR values to determine a cross-sectional area of the blood vessel interrogated by the LED-PD matrix. In this way, the curvilinear relationship between the RoR values corresponding to the optical paths formed by LED-PD pairs in the LED matrix and the centers of the optical paths across the diameter of the blood vessel being interrogated may be used to determine a cross-sectional area of the blood vessel. The comparison is achieved as described above by curve-fitting the RoR values measured for an LED-PD matrix and plotting the curve against the plurality of reference curvilinear relationships that may be plotted using reference measurements for blood vessels with different blood vessel diameters. The comparison of the RoR curvilinear relationship with the plurality of reference curvilinear relationships may also be performed using a lookup table, performing an algorithmic curve fitting, machine learning, or any combination thereof.

At steps 822 to 826, the analysis described with reference to FIGS. 8A and 8B may be used to measure selected blood metrics. To illustrate one example, once a set of RoR values has been curve-fit and aligned with one of the reference curves (curvet to curve8), the peak RoR value of the measured curve may be compared with the reference curve peaks (at 100%) to determine the V-offset at step 822. At step 824, the AC-to-DC components from table 540 (for example) in FIG. 5B may be processed to generate center column based RoRs. In an example implementation, the center column based RoRs may be either table 550 or table 560 and may be configured for use with a transfer function for a blood metric. In this example, a transfer function for HCT concentration may be defined at step 826 as [Hct]=ƒ (RoR_center_col) where the LED-PD matrix is positioned so that the center column is aligned with the blood vessel being interrogated. If the LED-PD matrix used for RoR measurements is not aligned with the blood vessel, the peak RoR value resulting from curve fitting the measured RoR values may be greater than 100%. In this case, the RoR peak value will be x>100% of the RoR center column. The percentages may be compared and used in [Hct]=ƒ (x*RoR_center_col).

It is noted that the example described with reference to FIG. 8A relates to determining an Hct concentration. Similar solutions may be used to determine other blood metrics.

EXAMPLE EMBODIMENTS

In view of the above, system and methods for monitoring blow metrics and/or for determining blood vessel geometric properties include the following:

Example 1: A system for monitoring blood flow metrics comprising:
 a patch of a flexible substrate configured to attach to an area of skin over a blood vessel;
 a plurality of light emitting diodes (LEDs) arranged on the substrate to form a R×C matrix and a row of C photodetectors (PDs) disposed on the substrate substantially in parallel with R rows of LEDs extending to form C columns substantially co-linear with each photodetector;
 an optical signal interface mounted on the substrate and configured to drive each LED for an on-period and to input an optical signal at one of the photodetectors during the on-period to receive an intensity measurement for an optical path, OPrc, formed by LEDs in rows r=1 to R in columns c=1 to C and the photodetector receiving the optical signal;
 a processing system comprising a memory for storing program instructions for execution by the processing system to:
 determine an AC component, Irc,AC, and a DC component, Irc,DC, as a function of a plurality of intensity measurements, Irc, for each optical path, OPrc, over a period of time;
 determine an AC-to-DC component ratio, $$R_{r,c} = \frac{I_{rc,AC}}{I_{rc,DC}},$$

for each optical path;
 determine a plurality of ratio-of-ratios, RoR values, by dividing a first plurality of selected AC-to-DC component ratios by a second plurality of selected AC to DC component ratios; and
 using at least a subset of the RoR values to determine a biological metric.

Example 2: The system of example 1 where the processing system is configured to determine the plurality of RoRs by dividing AC to DC component ratios in each row of AC to DC component ratios by the AC to DC component ratios in a row of AC to DC component ratios corresponding to the optical paths for a nearest LED row nearest to the row of photodetectors.

Example 3: The system of example 1 where the processing system is configured to:
 determine the plurality of RoRs by:
 dividing AC to DC component ratios in a row of AC to DC component ratios corresponding to the optical paths for a nearest LED row nearest to the row of photodetectors by themselves, and
 dividing AC to DC component ratios in each row starting with a second row by AC to DC component ratios in a next further row of AC to DC component ratios.

Example 4: The system of example 1 where:
 the plurality of LEDs is a plurality of infrared (IR) LEDs emitting infrared light;

the memory of the processing system includes program instructions for execution by the processing system to:
in using at least the subset of RoR values to determine the biological metric, the biological metric is hematocrit concentration, Hct, determined using:
Hct=F(RoR'), where F is a transfer function that correlates a range of RoR values to a range of hematocrit concentration values based on reference hematocrit concentrations determined from a plurality of reference RoR values measured using a reference hematocrit measurement system, and where RoR' is at least a subset of RoR values.

Example 5: The system of example 4 where the subset of RoR values includes RoR values corresponding to a column of LEDs.

Example 6: The system of example 4 where the subset of RoR values includes an RoR value selected by identifying a maximum RoR value.

Example 7: The system of example 4 where the RoR' values include a set of RoR values corresponding to all of the R×C LEDs.

Example 8: The system of example 4 where the RoR' values include a set of RoR values corresponding to all of the R×C LEDs, and the processing system is configured to surface fit the RoR' values in accordance with the transfer function.

Example 9: The system of example 4 where the transfer function, F, fits a second-order polynomial to the RoR' value to determine the hematocrit concentration.

Example 10: The system of example 8 where before measuring intensities, the transfer function F is determined using $Hct=aR^2+bR+c$, where parameters a, b, and c are determined from reference values of R=RoR to determine known values of Hct.

Example 11: The system of example 1 where:
the plurality of LEDs is a plurality of infrared (IR) LEDs for emitting light at a first wavelength in the infrared, the system further including a plurality of red LEDs for emitting light at a second wavelength in the red,
where each of the plurality of red LEDs is arranged on the substrate adjacent to each of the plurality of IR LEDs in the R×C matrix,
where the optical signal interface is configured to drive each IR LED and each red LED independently to form independent IR and red optical paths, $OP_{IR,r,c}$ and $OP_{red,r,c}$,
where the processing system is configured to measure an oxygen saturation metric by:
receiving a plurality of red intensity measurements, $I_{red,rc}$, corresponding to the optical paths, $OP_{red,rc}$, and a plurality of IR intensity measurements, $I_{IR,rc}$, corresponding to the optical paths, $OP_{IR,rc}$, for a period of time to receive a plurality of intensity measurements for each optical path at each wavelength;
determining a red AC component, $I_{red,rc,DC}$, and a red DC component, $I_{red,rc,DC}$, as a function of the plurality of intensity measurements, $I_{rc}$, for each red optical path, $OP_{red,rc}$, over the period of time;
determining an IR AC component, $I_{IR,rc,AC}$, and an IR DC component, $I_{IR,rc,DC}$, as a function of the plurality of intensity measurements, $I_{rc}$, for each IR optical path, $OP_{IR,rc}$, over the period of time;
determining a red AC-to-DC component ratio, $$R_{red,r,c} = \frac{I_{red,rc,ac}}{I_{red,rc,dc}},$$

for each red optical path;
determining an IR AC-to-DC component ratio, $$R_{IR,r,c} = \frac{I_{IR,rc,ac}}{I_{IR,rc,dc}},$$

for each IR optical path;
determining a plurality of composite ratio-of-ratios by dividing each of either red or IR AC-to-DC component ratios by each of either IR or red AC-to-DC component ratios until all of the red and IR AC-to-DC components are incorporated;
determining a plurality of ratio-of-ratios, RoR values, by dividing a first plurality of selected composite ratio-of-ratios by a second plurality of selected composite ratio-of-ratios; and
using at least a subset of the RoR values to determine a biological metric.

Example 12: The system of example 11 where the at least a subset of RoR values is used to determine the oxygen saturation, SpO2, according to $SpO_2=F(RoR')$, where F is a transfer function that correlates a range of RoR values to a range of oxygen saturation values based on reference oxygen saturation concentrations determined from the at least a subset of RoR values measured using a reference oxygen saturation measurement system.

Example 13: The system of example 12 where the transfer function, F, fits a second-order polynomial to the RoR' values to determine the oxygen saturation concentration.

Example 14: The system of example 13 where before measuring intensities, the transfer function F is determined using $SpO_2=aR^2+bR+c$, where parameters a, b, and c are determined from reference values of R=RoR to determine known values of $SpO_2$.

Example 15: The system of example 1 where the patch includes a communication interface mounted on the substrate and configured to communicate the plurality of intensities to the processing system operating on one or more networked computing devices.

Example 16: The system of example 1 where the patch includes the processing system mounted on the substrate of the patch and a communication interface configured to communicate biological metrics over a network.

Example 17: A system for determining geometric properties of a blood vessel comprising:
a patch of a flexible substrate configured to attach to an area of skin over the blood vessel;
a plurality of light emitting diodes (LEDs) arranged on the substrate to form a R×C matrix and a row of C photodetectors (PDs) disposed on the substrate substantially in parallel with R rows of LEDs extending to form C columns substantially co-linear with each photodetector;
an optical signal interface mounted on the substrate and configured to drive each LED for an on-period and to input an optical signal at one of the photodetectors during the on-period to receive an intensity measurement for an optical path, $OP_{rc}$, formed by LEDs in rows r=1 to R in columns c=1 to C and the photodetector receiving the optical signal;

a processing system comprising a memory for storing program instructions for execution by the processing system to:
    determine an AC component, $I_{rc,AC}$, and a DC component, $I_{rc,DC}$, as a function of a plurality of intensity measurements, $I_{rc}$, received for each optical path, $OP_{rc}$, over a period of time;
    determine an AC-to-DC component ratio, $$R_{r,c} = \frac{I_{rc,AC}}{I_{rc,DC}},$$

for each optical path;
    determine a plurality of ratio-of-ratios by dividing each AC-to-DC component ratio in each row by a high reference AC to DC component ratio until at least one row of the AC-to-DC component ratios are incorporated in the plurality of ratio-of-ratios;
    identify an optimal row of ratio-of-ratios corresponding to a row of optical paths that most intersect the blood vessel;
    correlate each ratio-of-ratios in the optimal row to a distance between the optical path of the corresponding ratio-of-ratio and a center column;
    identify a RoR curvilinear relationship for the optimal row of ratio-of-ratios;
    compare the RoR curvilinear relationship with a reference curvilinear relationship corresponding to a reference blood vessel having a known blood vessel diameter, the reference curvilinear relationship comprising values of percent ratios of AC-to-DC component ratios (reference RoRs) relative to a peak reference AC-to-DC component ratio, where each value corresponds to a distance between a center of the reference blood vessel and a reference optical path center of a reference optical path corresponding to each value of reference RoRs, where the reference optical paths are formed by the R×C matrix positioned such that a center column of the R×C matrix is centered over the reference blood vessel when intensities are measured for determination of the reference curvilinear relationship; and
    determine a cross-sectional area of the blood vessel from the known blood vessel diameter of the reference curvilinear relationship.

Example 18: The system of example 17 where identifying the optimal row includes calculating a weighted average of RoR values in each column, and using the weighted average RoR values as the RoRs in the optimal row.

Example 19: The system of example 17 where in comparing the RoR curvilinear relationship with the plurality of reference curvilinear relationships, determine an offset between the RoR curvilinear relationship and the reference curvilinear relationship, the offset corresponding to a distance between the center column of the R×C matrix and the center of the blood vessel indicated by a location of a peak in the reference curvilinear relationship.

Example 20: The system of example 17 where the reference curvilinear relationship is one of a plurality of curvilinear relationships each corresponding to a reference blood vessel having a known blood vessel diameter, where each reference curvilinear relationship comprises values of reference percent ratios of AC-to-DC component ratios (reference RoRs) relative to a peak reference AC-to-DC component ratio, where each value corresponds to a distance between a center of the reference blood vessel and a reference optical path center of a reference optical path corresponding to each value of reference RoRs, where the reference optical paths are formed by the R×C matrix positioned such that a center column of the R×C matrix is centered over each reference blood vessel when intensities are measured for determination of the plurality of reference curvilinear relationships, where the processor is configured to store the plurality of reference curvilinear relationships.

Example 21: The system of example 17 where in determining the plurality of ratio-of-ratios, the high reference AC-to-DC component ratio is the peak reference AC-to-DC component ratio.

Example 22: The system of example 17 where the comparing of the RoR curvilinear relationship with the reference curvilinear relationship comprises using a lookup table, performing an algorithmic curve fitting, machine learning, or any combination thereof.

Example 23: A system for monitoring blood flow metrics comprising
    a patch of a flexible substrate configured to attach to an area of skin over the blood vessel;
    a plurality of light emitting diodes (LEDs) arranged on the substrate to form a R×C matrix and a row of C photodetectors (PDs) disposed on the substrate substantially in parallel with R rows of LEDs extending to form C columns substantially co-linear with each photodetector;
    an optical signal interface mounted on the substrate and configured to drive each LED for an on-period and to input an optical signal at one of the photodetectors during the on-period to receive an intensity measurement for an optical path, $OP_{rc}$, formed by LEDs in rows r=1 to R in columns c=1 to C and the photodetector receiving the optical signal;
    a processing system comprising a memory for storing program instructions for execution by the processing system to:
        determine an AC component, $I_{rc,AC}$, and a DC component, $I_{rc,DC}$, as a function of a plurality of intensity measurements, $I_{rc}$, received for each optical path, $OP_{rc}$, over a period of time;
        determine an AC-to-DC component ratio, $$R_{r,c} = \frac{I_{rc,AC}}{I_{rc,DC}},$$

for each optical path;
        determine a first plurality of ratio-of-ratios by dividing each AC-to-DC component ratio in each row by a high reference AC-to-DC component ratio until at least one row of the AC-to-DC component ratios are incorporated in the first plurality of ratio-of-ratios;
        identify an optimal row of ratio-of-ratios corresponding to a row of optical paths that most intersect the blood vessel;
        correlate each ratio-of-ratios in the optimal row to a distance between the optical path of the corresponding ratio-of-ratio and a center column;
        identify a RoR curvilinear relationship for the optimal row of ratio-of-ratios;
        compare the RoR curvilinear relationship with a reference curvilinear relationship corresponding to a reference blood vessel having a known blood vessel diameter, the reference curvilinear relationship comprising values of percent ratios of AC-to-DC component ratios (reference RoRs) relative to a peak reference AC-to-DC component ratio, where each value corresponds to a distance between a center of the reference blood vessel and a reference optical path center of a reference optical path corresponding to each value of reference RoRs, where the reference optical paths are formed by the R×C matrix positioned such that a center column of the R×C matrix is centered over the reference blood vessel when intensities are measured for determination of the reference curvilinear relationship;

determine an offset between an RoR peak of the RoR curvilinear relationship and the reference peak of the reference curvilinear relationship;

identifying a peak RoR of the RoR curvilinear relationship above a peak reference RoR of the reference curvilinear relationship and determine a RoR correction factor as a percent RoR of the peak RoR of the RoR curvilinear relationship relative to the peak reference AC-to-DC component ratio; and determine a second plurality of ratio-of-ratios by dividing each AC-to-DC component ratio in each row by the AC-to-DC component ratio in other rows to determine an RoR for a center column of the second plurality of RoRs, where the RoR correction factor is used with the RoR for the center column of the second plurality of RoRs in a transfer function to determine a blood metric.

Example 24: The system of example 23 where the reference curvilinear relationship is one of a plurality of curvilinear relationships each corresponding to a reference blood vessel having a known blood vessel diameter, where each reference curvilinear relationship comprises values of reference percent ratios of AC-to-DC component ratios (reference RoRs) relative to a peak reference AC-to-DC component ratio, where each value corresponds to a distance between a center of the reference blood vessel and a reference optical path center of a reference optical path corresponding to each value of reference RoRs, where the reference optical paths are formed by the R×C matrix positioned such that a center column of the R×C matrix is centered over each reference blood vessel when intensities are measured for determination of the plurality of reference curvilinear relationships, where the processor is configured to store the plurality of reference curvilinear relationships.

Example 25: The system of example 23 where in determining the plurality of ratio-of-ratios, the high reference AC-to-DC component ratio is the peak reference AC-to-DC component ratio.

Example 26: The system of example 23 where the AC-to-DC component ratio for the optical path in a center column for each row.

Example 27: The system of example 23 where the comparing of the RoR curvilinear relationship with the reference curvilinear relationship comprises using a lookup table, performing an algorithmic curve fitting, machine learning, or any combination thereof.

Example 28: A method for monitoring blood flow metrics comprising:
driving at least one of R×C light emitting diodes (LEDs) for an on-period in a sequence, the R×C LEDs arranged along C columns and R rows on a substrate of a patch disposed above a blood vessel;
receiving a plurality of intensity measurements from at least one of C photodetectors during each on-period, each LED and photodetector operating during the on-period forming an optical path, where the C photodetectors are arranged along a photodetector row in parallel with the R rows of LEDs, each photodetector defining the C columns of LEDs extending from the photodetectors;
determining an AC component, $I_{rc,AC}$, and a DC component, $I_{rc,DC}$, as a function of the plurality of intensity measurements, $I_{rc}$, for each optical path, $OP_{rc}$, over the period of time;
determining a ratio of AC-to-DC components, $$R_{r,c} = \frac{I_{rc,AC}}{I_{rc,DC}},$$

for each optical path;
determining a plurality of ratio-of-ratios, RoR values, by dividing a first plurality of selected AC-to-DC component ratios by a second plurality of selected AC to DC component ratios; and
using at least a subset of the RoR values to determine a biological metric.

Example 29: The method of example 28 where:
the plurality of LEDs is a plurality of infrared (IR) LEDs emitting light at a wavelength in the infrared;
the method comprises:
in using at least the subset of RoR values to determine the biological metric, the biological metric is hematocrit concentration, Hct, determined using:
Hct=F(RoR'), where F is a transfer function that correlates a range of RoR values to a range of hematocrit concentration values based on reference hematocrit concentrations determined from a plurality of reference RoR values measured using a reference hematocrit measurement system, and where RoR' is at least a subset of RoR values.

Example 30: The method of example 29 where the transfer function, F, fits a second-order polynomial to the RoR' value to determine the hematocrit concentration.

Example 31: The method of example 30 where before measuring intensities, the method comprises determining the transfer function F using Hct=$aR^2$+bR+c, where parameters a, b, and c are determined from reference values of R=RoR to determine known values of Hct.

Example 32: The method of example 28 where:
the plurality of LEDs is a plurality of infrared (IR) LEDs for emitting light at a first wavelength in the infrared, the system further including a plurality of red LEDs for emitting light at a second wavelength in the red, where each of the plurality of red LEDs is arranged on the substrate adjacent to each of the plurality of IR LEDs in the R×C matrix,
where the optical signal interface is configured to drive each IR LED and each red LED independently to form independent IR and red optical paths, $OP_{IR,r,c}$ and $OP_{red,r,c}$,
where the method further comprises measuring an oxygen saturation metric by:
receiving a plurality of red intensity measurements, $I_{red,rc}$, corresponding to the optical paths, $OP_{red,rc}$, and a plurality of IR intensity measurements, $I_{IR,rc}$, corresponding to the optical paths, $OP_{IR,rc}$, for a period of time to receive a plurality of intensity measurements for each optical path at each wavelength;

determining a red AC component, $I_{red,rc,AC}$, and a red DC component, $I_{red,rc,DC}$, as a function of the plurality of intensity measurements, $I_{rc}$, for each red optical path, $OP_{red,rc}$, over the period of time;

determining an IR AC component, $I_{IR,rc,AC}$, and an IR DC component, $I_{IR,rc,DC}$, as a function of the plurality of intensity measurements, $I_{rc}$, for each IR optical path, $OP_{IR,rc}$, over the period of time;

determining a red AC-to-DC component ratio, $$R_{red,r,c} = \frac{I_{red,rc,AC}}{I_{red,rc,DC}},$$

for each red optical path;

determining an IR AC-to-DC component ratio $$R_{IR,r,c} = \frac{I_{IR,rc,AC}}{I_{IR,rc,DC}},$$

for each IR optical path;

determining a plurality of composite ratio-of-ratios by dividing each of either red or IR AC-to-DC component ratios by each of either IR or red AC-to-DC component ratios until all of the red and IR AC-to-DC components are incorporated;

determining a plurality of ratio-of-ratios, RoR values, by dividing a first plurality of selected composite ratio-of-ratios by a second plurality of selected composite ratio-of-ratios; and using at least a subset of the RoR values to determine a biological metric.

Example 33: The method of example 28 where the at least a subset of RoR values is used to determine the oxygen saturation, SpO2, according to $SpO_2 = F(RoR')$, where F is a transfer function that correlates a range of RoR values to a range of oxygen saturation values based on reference oxygen saturation concentrations determined from the at least a subset of RoR values measured using a reference oxygen saturation measurement system.

Example 34: The method of example 33 where the transfer function, F, fits a second-order polynomial to the RoR' value to determine the oxygen saturation concentration.

Example 35: The method of example 33 where before measuring intensities, the method comprising determining the transfer function F using $SpO_2 = aR^2 + bR + c$, where parameters a, b, and c are determined from reference values of R=RoR to determine known values of $SpO_2$.

Example 36: A method for determining geometric properties of a blood vessel comprising:

driving at least one of R×C light emitting diodes (LEDs) for an on-period in a sequence, the R×C LEDs arranged along C columns and R rows on a substrate of a patch disposed above a blood vessel;

receiving a plurality of intensity measurements from at least one of C photodetectors during each on-period, each LED and photodetector operating during the on-period forming an optical path, where the C photodetectors are arranged along a photodetector row in parallel with the R rows of LEDs, each photodetector defining the C columns of LEDs extending from the photodetectors;

determining an AC component, $I_{rc,AC}$, and a DC component, $I_{rc,DC}$, as a function of a plurality of intensity measurements, $I_{rc}$, received for each optical path, $OP_{rc}$, over a period of time;

determining an AC-to-DC component ratio, $$R_{r,c} = \frac{I_{rc,AC}}{I_{rc,DC}},$$

for each optical path;

determining a plurality of ratio-of-ratios by dividing each AC-to-DC component ratio in each row by a high reference AC to DC component ratio until at least one row of the AC-to-DC component ratios are incorporated in the plurality of ratio-of-ratios;

identifying an optimal row of ratio-of-ratios corresponding to a row of optical paths that most intersect the blood vessel;

correlating each ratio-of-ratios in the optimal row to a distance between the optical path of the corresponding ratio-of-ratio and a center column;

identifying a RoR curvilinear relationship for the optimal row of ratio-of-ratios;

comparing the RoR curvilinear relationship with a reference curvilinear relationship corresponding to a reference blood vessel having a known blood vessel diameter, the reference curvilinear relationship comprising values of percent ratios of AC-to-DC component ratios (reference RoRs) relative to a peak reference AC-to-DC component ratio, where each value corresponds to a distance between a center of the reference blood vessel and a reference optical path center of a reference optical path corresponding to each value of reference RoRs, where the reference optical paths are formed by the R×C matrix positioned such that a center column of the R×C matrix is centered over the reference blood vessel when intensities are measured for determination of the reference curvilinear relationship; and determining a cross-sectional area of the blood vessel from the known blood vessel diameter of the reference curvilinear relationship.

Example 37: The system of example 36 where identifying the optimal row includes calculating a weighted average of RoR values in each column, and using the weighted average RoR values as the RoRs in the optimal row.

Example 38: The method of example 36 where in comparing the RoR curvilinear relationship with the plurality of reference curvilinear relationships, determining an offset between the RoR curvilinear relationship and the reference curvilinear relationship, the offset corresponding to a distance between the center column of the R×C matrix and the center of the blood vessel indicated by a location of a peak in the reference curvilinear relationship.

Example 39: The method of example 36 where the reference curvilinear relationship is one of a plurality of curvilinear relationships each corresponding to a reference blood vessel having a known blood vessel diameter, where each reference curvilinear relationship comprises values of reference percent ratios of AC-to-DC component ratios (reference RoRs) relative to a peak reference AC-to-DC component ratio, where each value corresponds to a distance between a center of the reference blood vessel and a reference optical path center of a reference optical path corresponding to each value of reference RoRs, where the reference optical paths are formed by the R×C matrix positioned such that a center column of the R×C matrix is centered over each reference blood vessel when intensities are measured for determination of the plurality of reference curvilinear relationships, the method further storing the plurality of reference curvilinear relationships.

Example 40: The method of example 37 where in determining the plurality of ratio-of-ratios, the high reference AC-to-DC component ratio is the peak reference AC-to-DC component ratio.

Example 41: The method of example 37 where the comparing of the RoR curvilinear relationship with the reference curvilinear relationship comprises using a lookup table, performing an algorithmic curve fitting, machine learning, or any combination thereof.

Example 42: A method for monitoring blood flow metrics comprising driving at least one of R×C light emitting diodes (LEDs) for an on-period in a sequence, the R×C LEDs arranged along C columns and R rows on a substrate of a patch disposed above a blood vessel;
receiving a plurality of intensity measurements from at least one of C photodetectors during each on-period, each LED and photodetector operating during the on-period forming an optical path, where the C photodetectors are arranged along a photodetector row in parallel with the R rows of LEDs, each photodetector defining the C columns of LEDs extending from the photodetectors;
determining an AC component, $I_{rc,AC}$, and a DC component, $I_{rc,DC}$, as a function of a plurality of intensity measurements, $I_{rc}$, received for each optical path, $OP_{rc}$, over a period of time;
determining an AC-to-DC component ratio, $$R_{r,c} = \frac{I_{rc,AC}}{I_{rc,DC}},$$

for each optical path;
determining a first plurality of ratio-of-ratios by dividing each AC-to-DC component ratio in each row by a high reference AC-to-DC component ratio until at least one row of the AC-to-DC component ratios are incorporated in the first plurality of ratio-of-ratios;
identifying an optimal row of ratio-of-ratios corresponding to a row of optical paths that most intersect the blood vessel;
correlating each ratio-of-ratios in the optimal row to a distance between the optical path of the corresponding ratio-of-ratio and a center column;
identifying a RoR curvilinear relationship for the optimal row of ratio-of-ratios;
comparing the RoR curvilinear relationship with a reference curvilinear relationship corresponding to a reference blood vessel having a known blood vessel diameter, the reference curvilinear relationship comprising values of percent ratios of AC-to-DC component ratios (reference RoRs) relative to a peak reference AC-to-DC component ratio, where each value corresponds to a distance between a center of the reference blood vessel and a reference optical path center of a reference optical path corresponding to each value of reference RoRs, where the reference optical paths are formed by the R×C matrix positioned such that a center column of the R×C matrix is centered over the reference blood vessel when intensities are measured for determination of the reference curvilinear relationship;
determining an offset between an RoR peak of the RoR curvilinear relationship and the reference peak of the reference curvilinear relationship;
identifying a peak RoR of the RoR curvilinear relationship above a peak reference RoR of the reference curvilinear relationship and determine a RoR correction factor as a percent RoR of the peak RoR of the RoR curvilinear relationship relative to the peak reference AC-to-DC component ratio; and
determining a second plurality of ratio-of-ratios by dividing each AC-to-DC component ratio in each row by the AC-to-DC component ratio in other rows to determine an RoR for a center column of the second plurality of RoRs, where the RoR correction factor is used with the RoR for the center column of the second plurality of RoRs in a transfer function to determine a blood metric.

Example 43: The system of example 42 where identifying the optimal row includes calculating a weighted average of RoR values in each column, and using the weighted average RoR values as the RoRs in the optimal row.

Example 44: The method of example 42 where the reference curvilinear relationship is one of a plurality of curvilinear relationships each corresponding to a reference blood vessel having a known blood vessel diameter, where each reference curvilinear relationship comprises values of reference percent ratios of AC-to-DC component ratios (reference RoRs) relative to a peak reference AC-to-DC component ratio, where each value corresponds to a distance between a center of the reference blood vessel and a reference optical path center of a reference optical path corresponding to each value of reference RoRs, where the reference optical paths are formed by the R×C matrix positioned such that a center column of the R×C matrix is centered over each reference blood vessel when intensities are measured for determination of the plurality of reference curvilinear relationships, the method further comprising storing the plurality of reference curvilinear relationships.

Example 45: The method of example 42 where in determining the plurality of ratio-of-ratios, the high reference AC-to-DC component ratio is the peak reference AC-to-DC component ratio.

Example 46: The method of example 42 where the AC-to-DC component ratio for the optical path in a center column for each row.

Example 47: The method of example 42 where the comparing of the RoR curvilinear relationship with the reference curvilinear relationship comprises using a lookup table, performing an algorithmic curve fitting, machine learning, or any combination thereof.

The disclosure provided herein describes features in terms of preferred and exemplary embodiments thereof. Numerous other embodiments, modifications and variations within the scope and spirit of the appended claims will occur to persons of ordinary skill in the art from a review of this disclosure.

What is claimed is:

1. A system for monitoring blood flow metrics comprising:
a patch of a flexible substrate configured to attach to an area of skin over a blood vessel;
a plurality of light emitting diodes (LEDs) arranged on the substrate to form a R×C matrix and a row of C photodetectors (PDs) disposed on the substrate substantially in parallel with R rows of LEDs extending to form C columns substantially co-linear with each photodetector;
an optical signal interface mounted on the substrate and configured to drive each LED for an on-period and to input an optical signal at one of the photodetectors during the on-period to receive an intensity measurement for an optical path, $OP_{rc}$, formed by LEDs in rows r=1 to R in columns c=1 to C and the photodetector receiving the optical signal;

a processing system comprising a memory for storing program instructions for execution by the processing system to:

determine an AC component, $I_{rc,AC}$, and a DC component, $I_{rc,DC}$, as a function of a plurality of intensity measurements, $I_{rc}$, for each optical path, $OP_{rc}$, over a period of time;

determine an AC-to-DC component ratio, R_(r,c)=I_(rc,AC)/I_(rc,DC), for each optical path;

determine a plurality of ratio-of-ratios, RoR values, by dividing a first plurality of selected AC-to-DC component ratios by a second plurality of selected AC to DC component ratios; and using at least a subset of the RoR values to determine a biological metric;

where the processing system is configured to:
determine the plurality of RoRs by dividing AC to DC component ratios in each row of AC to DC component ratios by the AC to DC component ratios in a row of AC to DC component ratios corresponding to the optical paths for a nearest LED row nearest to the row of photodetectors.

2. A system for monitoring blood flow metrics comprising:

a patch of a flexible substrate configured to attach to an area of skin over a blood vessel;

a plurality of light emitting diodes (LEDs) arranged on the substrate to form a R×C matrix and a row of C photodetectors (PDs) disposed on the substrate substantially in parallel with R rows of LEDs extending to form C columns substantially co-linear with each photodetector;

an optical signal interface mounted on the substrate and configured to drive each LED for an on-period and to input an optical signal at one of the photodetectors during the on-period to receive an intensity measurement for an optical path, $OP_{rc}$, formed by LEDs in rows r=1 to R in columns c=1 to C and the photodetector receiving the optical signal;

a processing system comprising a memory for storing program instructions for execution by the processing system to:

determine an AC component, $I_{rc,AC}$, and a DC component, $I_{rc,DC}$, as a function of a plurality of intensity measurements, $I_{rc}$, for each optical path, $OP_{rc}$, over a period of time;

determine an AC-to-DC component ratio, R_(r,c)=I_(rc,AC)/I_(rc,DC), for each optical path;

determine a plurality of ratio-of-ratios, RoR values, by dividing a first plurality of selected AC-to-DC component ratios by a second plurality of selected AC to DC component ratios; and using at least a subset of the RoR values to determine a biological metric;

where the processing system is configured to:
determine the plurality of RoRs by:
dividing AC to DC component ratios in a row of AC to DC component ratios corresponding to the optical paths for a nearest LED row nearest to the row of photodetectors by themselves, and dividing AC to DC component ratios in each row starting with a second row by AC to DC component ratios in a next further row of AC to DC component ratios.

3. A system for monitoring blood flow metrics comprising:

a patch of a flexible substrate configured to attach to an area of skin over a blood vessel;

a plurality of light emitting diodes (LEDs) arranged on the substrate to form a R×C matrix and a row of C photodetectors (PDs) disposed on the substrate substantially in parallel with R rows of LEDs extending to form C columns substantially co-linear with each photodetector;

an optical signal interface mounted on the substrate and configured to drive each LED for an on-period and to input an optical signal at one of the photodetectors during the on-period to receive an intensity measurement for an optical path, $OP_{rc}$, formed by LEDs in rows r=1 to R in columns c=1 to C and the photodetector receiving the optical signal;

a processing system comprising a memory for storing program instructions for execution by the processing system to:

determine an AC component, $I_{rc,AC}$, and a DC component, $I_{rc,DC}$, as a function of a plurality of intensity measurements, $I_{rc}$, for each optical path, $OP_{rc}$, over a period of time;

determine an AC-to-DC component ratio, $$R_{r,c} = \frac{I_{rc,AC}}{I_{rc,DC}},$$

for each optical path;

determine a plurality of ratio-of-ratios, RoR values, by dividing a first plurality of selected AC-to-DC component ratios by a second plurality of selected AC to DC component ratios; and using at least a subset of the RoR values to determine a biological metric;

where the plurality of LEDs is a plurality of infrared (IR) LEDs emitting infrared light;

the memory of the processing system includes program instructions for execution by the processing system using at least the subset of RoR values to determine the biological metric, the biological metric is hematocrit concentration, Hct, determined using:

Hct=F(RoR'), where F is a transfer function that correlates a range of RoR values to a range of hematocrit concentration values based on reference hematocrit concentrations determined from a plurality of reference RoR values measured using a reference hematocrit measurement system, and where RoR' is at least a subset of RoR values.

4. The system of claim 3, where the subset of RoR values includes RoR values corresponding to a column of LEDs.

5. The system of claim 3, where:
the RoR' values include a set of RoR values corresponding to all of the R×C LEDs.

6. The system of claim 3, where the RoR' values include a set of RoR values corresponding to all of the R×C LEDs, and the processing system is configured to:
surface fit the RoR' values in accordance with the transfer function.

7. The system of claim 3, where the transfer function, F, fits a second-order polynomial to the RoR' value to determine the hematocrit concentration.

8. The system of claim 7, where before measuring intensities, the transfer function F is determined using $Hct=aR^2+bR+c$, where parameters a, b, and c are determined from reference values of R=RoR to determine known values of Hct.

9. A system for monitoring blood flow metrics comprising:
- a patch of a flexible substrate configured to attach to an area of skin over a blood vessel;
- a plurality of light emitting diodes (LEDs) arranged on the substrate to form a R×C matrix and a row of C photodetectors (PDs) disposed on the substrate substantially in parallel with R rows of LEDs extending to form C columns substantially co-linear with each photodetector;
- an optical signal interface mounted on the substrate and configured to drive each LED for an on-period and to input an optical signal at one of the photodetectors during the on-period to receive an intensity measurement for an optical path, $OP_{rc}$, formed by LEDs in rows r=1 to R in columns c=1 to C and the photodetector receiving the optical signal;
- a processing system comprising a memory for storing program instructions for execution by the processing system to:
  - determine an AC component, $I_{rc,AC}$, and a DC component, $I_{rc,DC}$, as a function of a plurality of intensity measurements, $I_{rc}$, for each optical path, $OP_{rc}$, over a period of time;
  - determine an AC-to-DC component ratio, $R\_(r,c)=I\_(rc,AC)/I\_(rc,DC)$, for each optical path;
  - determine a plurality of ratio-of-ratios, RoR values, by dividing a first plurality of selected AC-to-DC component ratios by a second plurality of selected AC to DC component ratios; and
  - using at least a subset of the RoR values to determine a biological metric;
- the plurality of LEDs is a plurality of infrared (IR) LEDs for emitting light at a first wavelength in the infrared, the system further including a plurality of red LEDs for emitting light at a second wavelength in the red,
- where each of the plurality of red LEDs is arranged on the substrate adjacent to each of the plurality of IR LEDs in the R×C matrix,
- where the optical signal interface is configured to drive each IR LED and each red LED independently to form independent IR and red optical paths, $OP_{IR,r,c}$ and $OP_{red,r,c}$,
- where the processing system is configured to measure an oxygen saturation metric by:
  - receiving a plurality of red intensity measurements, $I_{red,rc}$, corresponding to the optical paths, $OP_{red,rc}$, and a plurality of IR intensity measurements, $I_{IR,rc}$, corresponding to the optical paths, $OP_{IR,rc}$, for a period of time to receive a plurality of intensity measurements for each optical path at each wavelength;
  - determining a red AC component, $I_{red,rc,DC}$, and a red DC component, $I_{red,rc,DC}$, as a function of the plurality of intensity measurements, $I_{rc}$, for each red optical path, $OP_{red,rc}$, over the period of time;
  - determining an IR AC component, $I_{IR,rc,AC}$, and an IR DC component, $I_{IR,rc,DC}$, as a function of the plurality of intensity measurements, $I_{rc}$, for each IR optical path, $OP_{IR,rc}$, over the period of time;
  - determining a red AC-to-DC component ratio, $$R_{red,r,c} = \frac{I_{red,rc,ac}}{I_{red,rc,dc}},$$

for each red optical path;
  - determining an IR AC-to-DC component ratio, $$R_{IR,r,c} = \frac{I_{IR,rc,ac}}{I_{IR,rc,dc}},$$

for each IR optical path;
  - determining a plurality of composite ratio-of-ratios by dividing each of either red or IR AC-to-DC component ratios by each of either IR or red AC-to-DC component ratios until all of the red and IR AC-to-DC components are incorporated;
  - determining a plurality of ratio-of-ratios, RoR values, by dividing a first plurality of selected composite ratio-of-ratios by a second plurality of selected composite ratio-of-ratios; and
  - using at least a subset of the RoR values to determine a biological metric.

10. The system of claim 9, where the at least a subset of RoR values is used to determine the oxygen saturation, SpO2, according to:
$SpO_2=F(RoR')$, where F is a transfer function that correlates a range of RoR values to a range of oxygen saturation values based on reference oxygen saturation concentrations determined from the at least a subset of RoR values measured using a reference oxygen saturation measurement system.

11. The system of claim 10, where the transfer function, F, fits a second-order polynomial to the RoR' values to determine the oxygen saturation concentration.

12. The system of claim 11, where before measuring intensities, the transfer function F is determined using $SpO_2=aR^2+bR+c$, where parameters a, b, and c are determined from reference values of R=RoR to determine known values of $SpO_2$.

13. The system of claim 1 where the patch includes a communication interface mounted on the substrate and configured to communicate the plurality of intensities to the processing system operating on one or more networked computing devices.

14. The system of claim 1 where the patch includes the processing system mounted on the substrate of the patch and a communication interface configured to communicate biological metrics over a network.

* * * * *